US008946167B2

(12) United States Patent
Hegedus et al.

(10) Patent No.: US 8,946,167 B2
(45) Date of Patent: Feb. 3, 2015

(54) PHARMACEUTICAL COMPOSITIONS CONTAINING PLASMA PROTEIN

(75) Inventors: Lajos Hegedus, Budapest (HU); Krisztina Krempels, Budapest (HU); Krisztina Paal, Budapest (HU); Gabor Petho, Budapest (HU)

(73) Assignee: Teva Pharmaceutical Industries Ltd., Petah Tikva (IL)

( * ) Notice: Subject to any disclaimer, the term of this patent is extended or adjusted under 35 U.S.C. 154(b) by 0 days.

(21) Appl. No.: 12/322,997

(22) Filed: Feb. 9, 2009

(65) Prior Publication Data
US 2010/0076008 A1     Mar. 25, 2010

Related U.S. Application Data

(60) Division of application No. 10/802,528, filed on Mar. 17, 2004, now Pat. No. 7,501,455, which is a continuation of application No. 09/299,562, filed on Apr. 27, 1999, now Pat. No. 6,743,826, which is a continuation of application No. PCT/HU98/00086, filed on Sep. 17, 1998.

(30) Foreign Application Priority Data

Sep. 18, 1997  (HU) ...................................... 9701554

(51) Int. Cl.
| | | |
|---|---|---|
| A61K 38/38 | (2006.01) | |
| A61P 35/00 | (2006.01) | |
| C07K 14/765 | (2006.01) | |
| A61K 9/00 | (2006.01) | |
| A61K 31/335 | (2006.01) | |
| A61K 31/337 | (2006.01) | |
| A61K 31/5513 | (2006.01) | |
| A61K 38/13 | (2006.01) | |
| A61K 38/20 | (2006.01) | |
| A61K 38/21 | (2006.01) | |
| A61K 47/42 | (2006.01) | |

(52) U.S. Cl.
CPC ............. *A61K 9/0019* (2013.01); *A61K 31/335* (2013.01); *A61K 31/337* (2013.01); *A61K 31/5513* (2013.01); *A61K 38/13* (2013.01); *A61K 38/20* (2013.01); *A61K 38/21* (2013.01); *A61K 47/42* (2013.01)
USPC .......... 514/19.3; 514/15.2; 530/363; 435/345

(58) Field of Classification Search
USPC ......................................................... 514/449
See application file for complete search history.

(56) References Cited

U.S. PATENT DOCUMENTS

| | | | |
|---|---|---|---|
| 4,842,856 A | 6/1989 | Hoederath et al. | |
| 5,356,927 A * | 10/1994 | Taraschi et al. ............... | 514/449 |
| 5,560,933 A | 10/1996 | Soon-Shiong et al. | |
| 5,621,001 A | 4/1997 | Canetta et al. | |
| 5,665,761 A | 9/1997 | Canetta et al. | |
| 5,670,537 A | 9/1997 | Canetta et al. | |
| 5,856,333 A * | 1/1999 | Cabri et al. ................... | 514/283 |
| 5,916,596 A * | 6/1999 | Desai et al. ................... | 424/489 |
| 6,652,884 B2 * | 11/2003 | Falciani ........................ | 424/489 |

FOREIGN PATENT DOCUMENTS

| | | |
|---|---|---|
| DE | 37 02 105 A1 | 8/1988 |
| EP | 0326 618 A1 | 8/1989 |
| HU | 198381 | 1/1987 |
| JP | 58-216126 | 12/1983 |
| WO | WO 98/14174 | 4/1998 |

(Continued)

OTHER PUBLICATIONS

"Guidance for Industry, Extended Release Oral Dosage Forms: Development. Evaluation, and Application of In Vitro/In Vivo Correlations", *U.S. Department of Health and Human Services, Food and Drug Administration, Center for Drug Evaluation and Research* (CDER) (Sep. 1997), 1-24.
Aarset et al., "A nurse with a rash on her neck", Ansquer et al., "Survival in early-onset BRCA1 breast-cancer patients", Shimomura et al., "Effects of Taxol on blood cells", Ashok et al., "Termination of pregnancy at 9-13 weeks' amenorrhoea with mifepristone and misoprostol", The Lancet (Aug. 15, 1998), 352(9127):540-542.
Bejinen et al., "Bioanalysis, Pharmacokinetics, and Pharmacodynamics of the Novel Anticancer Drug Paclitaxel (Taxol)", *Seminars in Oncology* (Oct. 1994), 21(5):53-62.

(Continued)

*Primary Examiner* — Elly-Gerald Stoica
(74) *Attorney, Agent, or Firm* — Kenyon & Kenyon LLP

(57) ABSTRACT

The invention is related to water-soluble products and pharmaceutical formulations in solid or liquid form mainly for parenteral use. They consist of or comprise a therapeutically active substance (having low aqueous solubility and a substantial binding affinity to plasma proteins) and a plasma protein fraction in controlled aggregation state, whereby the said active substance and the said protein fraction are bound to each other by way of non-covalent bonds. It also covers processes for the preparation of the product and pharmaceutical formulation by dissolving the water-insoluble active substance in a water-miscible, pharmaceutically acceptable solvent, combining said solution with the aqueous solution of a plasma protein fraction in controlled aggregation state whereby a true solution is obtained containing the said active substance and the said protein fraction bound together by way of non-covalent bonds. Optionally a further pharmaceutically acceptable auxiliary additive—such as a protein aggregation controller and/or a stabilizer—may be present. The organic solvent is eliminated by dialyzing, ultrafiltrating, diafiltrating and/or lyophilizing. The solid products consisting of the active substance and the protein are also protected. On optional dissolution in water clear, liquid compositions are obtained suitable for direct parenteral or other administration. Method of treatment is also covered. A series of water-insoluble substances is enlisted with appropriate protein fractions to be used.

8 Claims, 14 Drawing Sheets

(56) References Cited

FOREIGN PATENT DOCUMENTS

| WO | WO 98/28011 | | 7/1998 | |
|---|---|---|---|---|
| WO | WO/99/13914 | * | 3/1999 | ............. A61K 47/42 |

OTHER PUBLICATIONS

Eiseman et al., "Plasma pharmacokinetics and tissue distribution of paclitaxel in $DC_2F_1$ mice". *Cancer Chemotherapy and Pharmacology* (1994), 34; 465-471.

Guitton et al., "Quantitation of propofol in whole blood by gas chromatography-mass spectrometry", *Journal of Chromatography B: Biomedical Applications* (Jul. 21, 1995), 669:358-365.

Hallbach et al., "Determination of Lamotrigine, Carbamazepine and Carbamazepine Epoxide in Human Serum by Gas Chromatography Mass Spectrometry", *European Journal of Clinical Chemistry and Clinical Biochemistry* (Oct. 1997), 35(10):755-759.

Johansen et al., "Automated analysis of free and total concentrations of three antiepileptic drugs in plasma with on-line dialysis and high-performance liquid chromatography", *Journal of Chromatography B: Biomedical Applications* (Jul. 21, 1995) 669: 281-288.

Olah et al., "Molecular Mechanisms in the Antiproliferative Action of Taxol and Tiazofurin". *Anticancer Research—International Journal of Cancer Research and Treatment* (Sep.-Oct. 1996), 16:2469-2477.

Pavan et al., "Monitoring Propofol Serum Levels by Rapid and Sensitive Reversed-Phase High-Performance Liquid Chromatography During Prolonged Sedation in ICU Patients", *Chromatographic Science* (May 1992), 30(5):164-166.

Puls et al., "MicroTICAS—The Design of an Inexpensive Video-Based Microphotometer / Computer System for DNA Ploidy Studies", *Analytical and Quantitative Cytology Histology* (1986), 8(1):1-7.

Rivory et al., "Identification and Properties of a Major Plasma Metabolite of Irinotecan (CPT-11) Isolated from the Plasma of Patients", *Cancer Research* (Aug. 15, 1996), 56:3689-3694.

Rowinsky at al., "Taxol: A Novel Investigational Antimicrotubule Agent", *Journal of the National Cancer Institute* (Aug. 1990), 82(15):1247-1259.

Royer at al., "Paclitaxel Metabolites in Human Plasma and Urine: Identification of 6ÿ-Hydroxytaxol, 7-Epitaxol and Taxol Hydrolysis Products Using Liquid Chromatography/Atmospheric-pressure Chemical Ionization Mass Spectrometry", *Rapid Communications in Mass Spectrometry* (1995), 9:495-502.

Schäfer-Korting et al., "Influence of Serum Protein Binding on the In Vitro Activity of Antifugnal Agents", *Infection* (1995), 23(5):292-297.

Sottani et al., "Structural Characterization of Mono-and Dihydroxylated Metabolites of Paclitaxel in Rat Bile Using Liquid Chromatography / Ion Spray Tandem Mass Spectrometry", *Rapid Communications in Mass Spectrometry* (1997), 11:1025-1032.

Thomas et al., "15-Deoxyspergualin: A Novel Immunosuppressive Drug with Clinical Potential", *Annals of the New York Academy of Sciences* (1993) 685:175-192.

Patent Abstracts of Japan, Inaba Mitsuhara, JP58-216126, Dec. 15, 1983.

Paal et al., Eur. J. Biochem, (2001) 268:2197-2191.

Carter, Daniel C., et al., "Three-Dimensional Structure of Human Serum Albumin," Science, vol. 244, p. 1195-1198, 1989.

Bridonneau, P., et al., "Liquid Pasteurization of an Immunoglobulin Preparation without Stabilizer: Effects on its Biological and Biochemical Properties," Vox Sang 1996; 70:203-209.

* cited by examiner

FIG. 7A
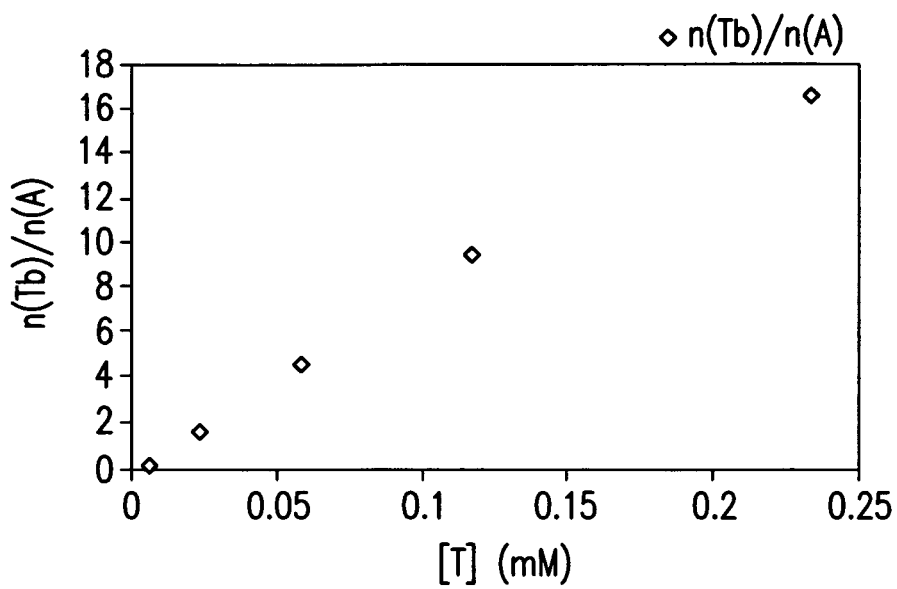
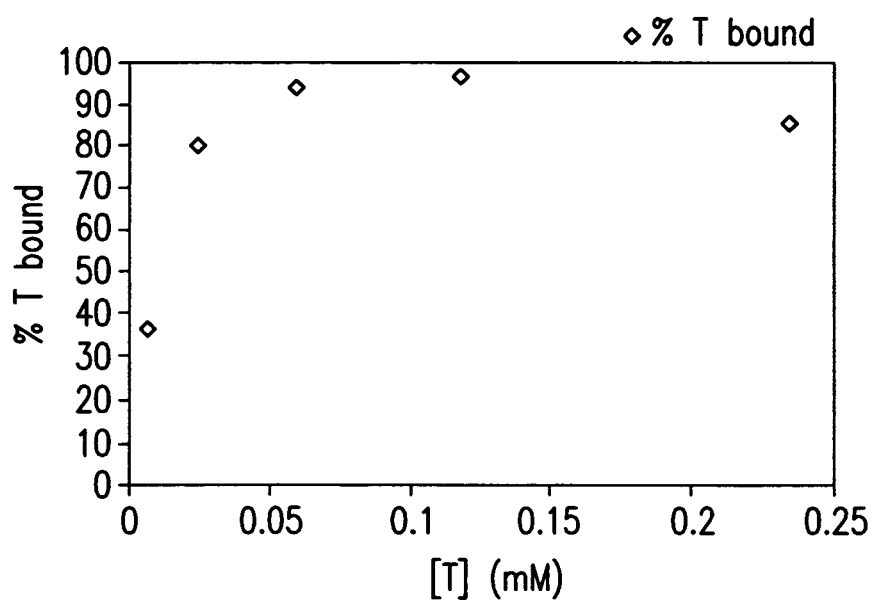
FIG. 7B

FIG. 8A
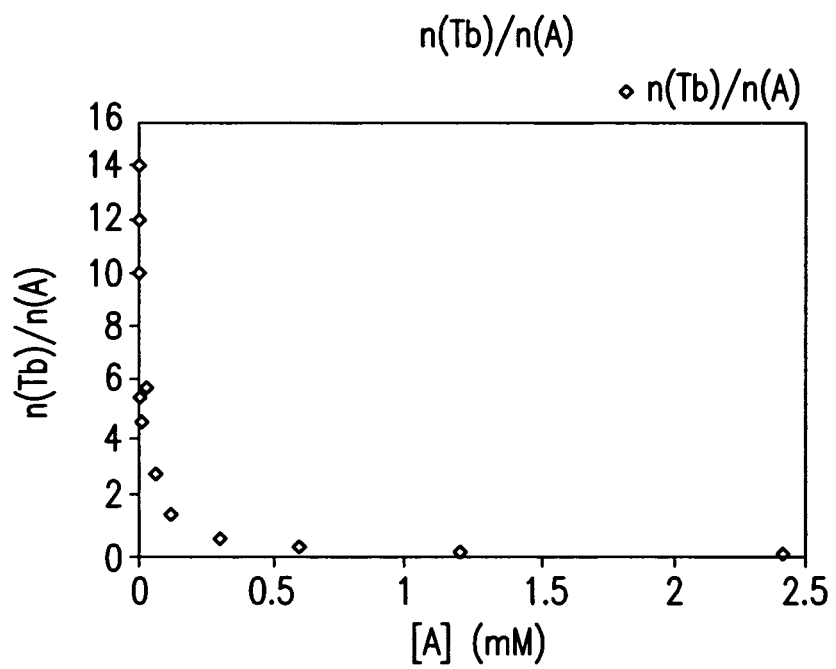
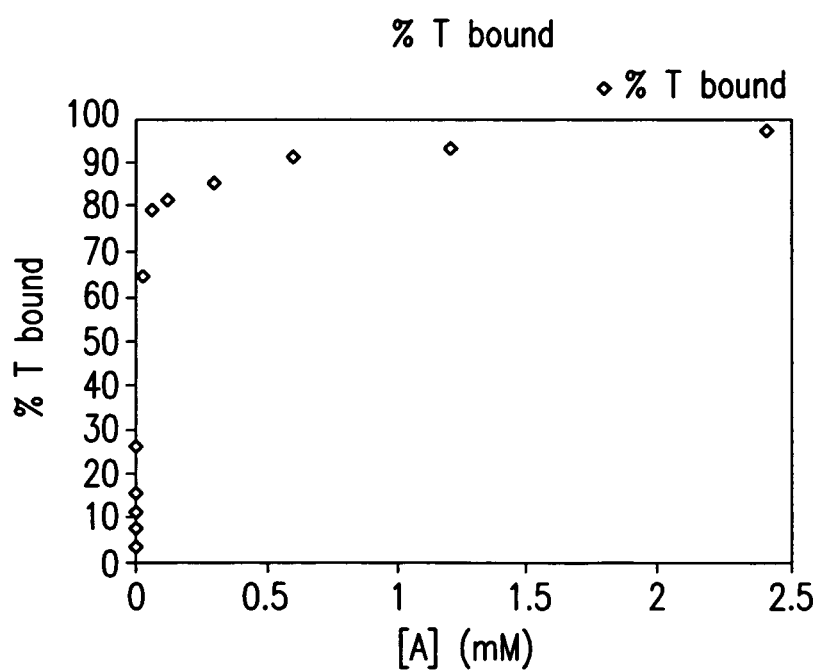
FIG. 8B

PHARMACEUTICAL COMPOSITIONS CONTAINING PLASMA PROTEIN

CROSS REFERENCE TO RELATED APPLICATIONS

This application is a divisional of U.S. patent application Ser. No. 10/802,528 filed Mar. 17, 2004, now U.S. Pat. No. 7,501,455 which is a continuation of U.S. patent application Ser. No. 09/299,562, now U.S. Pat. No. 6,793,826, filed Apr. 27, 1999, the disclosures of which are incorporated by reference herein in their entirety. U.S. patent application Ser. No. 09/299,562 is a continuation of PCT/HU98/000086, filed Sep. 17, 1998, which claims priority from Hungarian Patent Application HU P 97 01554, filed Sep. 18, 1997.

FIELD OF THE INVENTION

The present invention is related to a new method, products and formulations for delivery in therapeutic use of therapeutically active compounds having poor water solubility and substantial binding affinity to plasma proteins and processes for the preparations of such products and formulations.

More particularly first objects of the invention are products and pharmaceutical formulations in solid or liquid form mainly for parenteral use consisting of or comprising
   a) a therapeutically active substance having low aqueous solubility and a substantial binding affinity to plasma proteins (in the following "active substance") and
   b) a plasma protein fraction in controlled aggregation state whereby the said active substance and the said protein fraction are bound to each other by way of non-covalent bonds and
   c) optionally further pharmaceutically acceptable and mainly parenterally acceptable formulation additive(s)—such as water, stabilizer(s), protein aggregation controller(s).

The homogeneous solid state products of the invention consisting of the said protein and the said substance are water-soluble and their aqueous solutions can be used parenterally or can be used to prepare parenteral pharmaceuticals.

It is well known in the art that some biologically active compounds possess potent therapeutic activity but could never demonstrate their benefit because of their poor solubility in aqueous media. Some of them were never ever formulated while a few did not reach but the stage of the "phase I" clinical development. Some of them appear in "hardly biocompatible" formulations of relatively high toxicity caused by the materials used for formulation. A typical example for this is represented by the groups of taxones specifically paclitaxel which is a potent cytostatic the application of which however is reduced because of the toxicity of its known formulation in Klucel:tween 80 or Klucel and diluent 12, a 1:1 mixture of Cremaphor EL:ethanol. [Cancer Chemotherapy and Pharmacology (1994) 34:465-471; Journal of the National Cancer Institute (1990) 1247-1259). Cremaphor EL (polyoxyethylated castor oil) has inherent toxicity, causing vasodilatation, lethargy, hypotension etc. In order to decrease the toxic side-effect of the solvent and adjuvant, a series of special methods were suggested: application of very small doses over a long period of time, pre-medication before treatment etc. (U.S. Pat. No. 5,665,761; U.S. Pat. No. 5,621,001; U.S. Pat. No. 5,670,537 etc.) A further suggestion consisted in combination of the active substance with a dispersing agent contained within a protein walled shell (U.S. Pat. No. 5,560,933) which is formed by reacting the protein with oil such as soy bean oil—such formulations being proposed for paclitaxel and amphotericin. However even the latest literature comprises warnings on the course of application of e.g. paclitaxel (see e.g. "Guidance for Industry issued by the U.S. Department of Health and Human Service CDER September 1997, OGD-L-8) where—because of hypersensitivity reactions—all patients treated with paclitaxel should be premedicated with corticosteroids, diphenhydramine and $H_2$ antagonists.

It was further proposed to prepare parenteral formulations of certain water-insoluble dihydropyridins, by dissolving them in an organic solvent or in a mixture of an organic solvent with water and adding an aqueous HSP solution to said solution in order to minimise crystallisation of the insoluble active substance (Hungarian Patent No. 198381; DE Appl. 37 02105). The resulting liquid however was still not a clear solution.

BACKGROUND OF THE INVENTION

It is further known that some of the water-insoluble active substances possess a considerable affinity to protein or serum protein. Some literature is mentioned here for paclitaxel [Cancer Chem. and Pharm. (1994)34: 465-471]; miconazole, fluconazole, amphotericin B [Infection, 23 (5): 292-297 (1995) September]; carbamazepine [J. Chromatogr. B Biomed. Appl. 669(2): 281-288 (1995 Jul. 21]; azathioprine [Ann. N.Y. Acad. Sci, 685 (1993): 175-192], propofol [J. Chromatogr. Sci (1992): 164-166]. According to new literature [The Lancet vol. 352 (1998): 540-542] the drug Taxol® caused rouleaux formation of red cells and so did polyoxyethylated castor oil which served as the solvent of said drug. Some water-insoluble drugs were formulated using the toxic Cremaphor (cyclosporin, teniposide, paclitaxel, amphotericin B). To the best of our knowledge a series of highly active but water-insoluble drugs was not available so far on the market in parenteral, intravenous administration forms at all e.g. ritonavit, carbamazepine, camphotethine, azathiopine, miconazole, fluconazole etc.

Thus there is a need to solve the problem whereby therapeutically valuable water-insoluble substances can be administered in water-soluble form, preferably parenterally to a patient in need to be treated with said active ingredients.

SUMMARY OF THE INVENTION

The aim of this invention is to meet this requirement concerning practically water-insoluble active ingredients having a substantial binding affinity to plasma proteins.

BRIEF DESCRIPTION OF THE FIGURES

FIG. 7 shows the variation of paclitaxel concentration (with 0.08% HSA, 10% ethanol, 0.2 mg/ml paclitaxel). FIG. 7A shows a plot of n(Tb)/n(A); FIG. 7B shows a plot of % T bound.

FIG. 8 shows the variation of paclitaxel binding to HSA (with 0.004% 16% HSA, 20% ethanol, 0.2 paclitaxel). FIG. 8A shows a plot of n(Tb)/n(A); FIG. 8B shows a plot of % T bound.

DETAILED DESCRIPTION OF THE INVENTION

Figure 1:
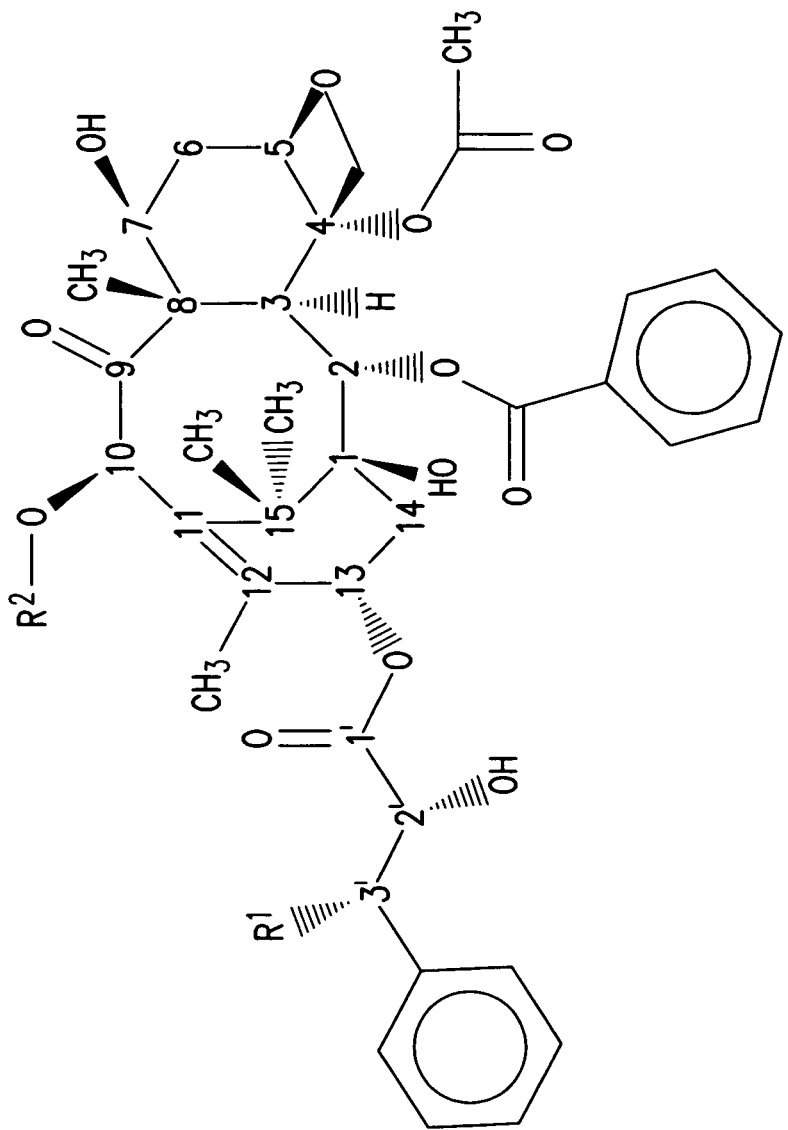
FIG. 1 represents a taxonoid of the general formula I.

The present invention is based on the recognition that binding the active substances to adequate proteins with non-covalent bonds before administration presents a new and highly potential delivery system for the administration of the active ingredients with poor water solubility. According to the invention homogeneous solid products are produced which are then dissolved in water whereby biocompatible, clear, aqueous solutions are obtained which are suitable for parenteral administration. Thus the invention presents a means to administer the desired water-insoluble active ingredients without introducing the toxic elements and in certain cases in a considerable more efficient dose than before.

Definitions used throughout this application which are henceforth not repeated:
$R^1$ represents tent. butyl-oxy-carboxylic acid amide or benzoyl amide;
$R^2$ represents hydrogen or any acyl group preferably acetyl;
Low water-solubility means that the solubility in water at room temperature<$1.10^{-4}$ M;
Substantial binding affinity to plasma proteins means that >90% of the substance is bound to the proteins in aqueous medium in spontaneous equilibrium at room temperature;
HSA human serum albumin,
WFI water for injection.

One object of the invention is a water-soluble human pharmaceutical formulation mainly for parenteral use containing a therapeutically active compound having low aqueous solubility and a substantial binding affinity to plasma proteins or a human plasma protein fraction in controlled aggregation state.

Other objects of the invention are water-soluble veterinary pharmaceutical formulations mainly for parenteral use containing a therapeutically active compound having low aqueous solubility and a substantial binding affinity to animal plasma proteins in controlled aggregation state.

The human or animal plasmae which can be present in the products and pharmaceutical formulations according to the invention and accordingly used in the methods to prepare the products and compositions can be any of the naturally occurring proteins or plasma fractions such as serum albumin, an immunoglubulin, glycoprotein, interferon and/or interleukin as well as the recombinant analogues of the same. Human and animal proteins can be used. In compounds and compositions intended for treatment of humans the natural human serum and the recombinant human serum proteins are preferred.

The practically water-insoluble active ingredients according to the invention comprise a wide range of compounds whereby the only limitation is that they have to show a substantial affinity to the plasma protein which is selected to be used. Examples for such active ingredients include the following groups of therapeutic agents: a cytostatic such as a taxonoide, antibiotic, vitamin, antiinflammatory, analgesic, anticonvulsant, immunosuppressant, antiepileptic, anxiolytic, hypnotic, antifungal agent, anticoagulant, lipid peroxidase inhibitor, coronary vasodilator, antiarrythmic agent, cardiotonic, uricosuric, antithrombotic, steroid hormone (progestogen, androgen, testogen) and/or photo sensitizer. Several active ingredients can be used at the same time after careful consideration and adaptation of the therapeutic doses and consideration of the binding affinities to the selected proteins which have to be able to meet such changed requirements.

According to an embodiment of the invention there are provided products and pharmaceutical formulations according to the above containing at least one of the following active substances: amphotericin B, an adriamicine analogue, apazone, azathioprine, bromazepam, camptothecin, carbamazepine, clonazepam, cyclosporine A, diazepam, dicumarol, digitoxine, dipyridamole, disopyramide, flunitrazepam, gemfibrozil, ketochlorin, ketoconazole, miconazole, niflumic acid, oxazepam, phenobarbital, phenytoin, progesterone, propofol, ritonavir, sulfinpyrazone, suprofene, tacrolimus, tamoxifen, taxonoid, testosterone, tirilazad, trioxsalen, valproic acid and/or warfarin.

A preferred embodiment of the invention consists in a product or formulation as described above containing a taxonoid of the general formula I.

Another preferred embodiment according to the invention contains or consists of paclitaxel and human serum albumin, immunoglobulin, glycoprotein, interferon and/or interleukin or some other human plasma protein fraction.

Further specially important representatives of the invention are homogeneous, solid, water-soluble products consisting of at least one active substance of the group amphotericin B, an adriamicine analogue, apazone, azathioprine, bromazepam, camptothecin, carbamazepine, clonazepam, cyclosporine A, diazepam, dicumarol, digitoxine, dipyridamole, disopyramide, flunitrazepam, gemfibrozil, ketochlorin, ketoconazole, miconazole, niflumic acid, oxazepam, phenobarbital, phenytoin, progesterone, propofol, ritonavir, sulfinpyrazone, suprofene, tacrolimus, tamdxifen, taxonoid, testosterone, tirilazad, trioxsalen, valproic acid and/or warfarin and also consisting of at least one protein of the group human serum albumin, immunoglobulin, glycoprotein, interferon and/or interleukin or some other natural or recombinant human plasma protein fraction where the said active substance and the said protein fraction are bound to each other by way of non-covalent bonds and wherein the molar ratio of the said active substance and the said protein fraction is within the range of 1:0.05 to 1:100, preferably of 1:0.1 to 1:50.

Preferred representatives of the above are the following homogeneous, solid, water-soluble products consisting of the following pairs of active substances and proteins:taxonoide of the general formula I—in the formula
$R^1$ represents tert. butyl-oxy-carboxylic acid amide or benzoyl amide,
$R^2$ represents hydrogen or any acyl group preferably acetyl—
and a plasma protein fraction;
paclitaxel and human serum albumin, recombinant human plasma albumin and/or γ-globulin;
amphotericin B and human serum albumin, recombinant human plasma albumin and/or γ-globulin;
camptothecin and human serum albumin, recombinant human plasma albumin and/or γ-globulin;
carbamazepin and human serum albumin, recombinant human plasma albumin and/or γ-globulin, cyclosporin A and human serum albumin, recombinant human plasma albumin and/or γ-globulin;

propofol and human serum albumin, recombinant human plasma albumin and/or γ-globulin.

It is clear from the above explanations that the invention covers the pharmaceutical formulations as above both in the solid state and also in the form of the aqueous solutions.

As it is related to their natural structure—more specifically to their chemical composition—the protein molecules tend to aggregate through their specific binding sites. The degree of aggregation depends on the parameters (temperature, composition, relative and absolute concentration of the components, consequently the pH, ion strength) of the solution where the protein is present.

The plasma proteins used according to the invention are preferably in a stabilized or controlled aggregation state. The aim is to avoid such aggregation of the proteins which would inhibit optimal binding of the active ingredient actually used. The unwanted aggregation of the proteins can be controlled by the presence of other molecules capable to occupy some or all of the binding sites on the macromolecules involved in the aggregation so as to avoid multiple protein-protein association. Some proteins are available on the market in a controlled aggregation state: containing stabilisers to avoid aggregation. This state however is not always the optimal state for entering into binding with the active substance we intend to use according to the invention.

According to the invention the term "controlled aggregation state" represents the best binding state when the protein is capable to bind the active substance exactly in the manner which is desired for the purpose aimed at. It is not necessarily the state when the maximum number of the active substance molecules are bound to the protein—but there are cases when the highest binding proportion is desirable.

That means that in some cases we have to remove other excipients from e.g. a commercially available serum albumin fraction, such as stabilisers, ionic components, etc. This might be the necessary starting step of the process when the method according to the invention is carried out. The required conditions to establish the proper aggregation stage strictly depends on the actual active substance and the relevant protein fraction.

Examples provided below demonstrate (e.g. paclitaxel and cyclosporine A) that they show a higher binding to a plasma protein fraction in the absence of other excipients (such as stabilisers, ionic components, salts etc.). However there are other active substances (e.g. amphotericin B and propofol) which did not show any interference with the binding of e.g. the protein stabilisers.

Thus the proper aggregation state of the protein used has to be established for each and every pair of active substance/protein which is used according to the present invention.

When using the pair paclitaxel and HSA: it is important to eliminate all stabilisers accompanying commercially available HSA: such as N-acetyl-D,L-tryptophane, alkali caprilates which were used to stabilize the protein during pasteurisation at 60° C. Amphothericin B or propofol can be bound to HSA also in the presence of these stabilisers. In certain instances, when the desired aggregation state could be reached by water, the other components had to be removed, following e.g. the procedure detailed below in one of the Examples.

The following aspects have to be considered for optimum combination of specific substances with specific plasma protein fractions according to the invention:

a) the characteristics of the binding site occupied by the substance on the protein;

b) possible other components present in the solution occupying the same binding site or even competing for it;

c) the physico-chemical conditions for the conformation of the actual binding site and the consequence to the binding;

d) known therapeutic aspects e.g.

i) paclitaxel on HSA having uric transport characteristics;

ii) paclitaxel on interleukines with proven therapeutic activity of the carrier;

iii) cyclosporin A on gamma immunoglobulin with proven therapeutic activity of the carrier;

iv) ritonavir on gamma immunoglobulin with proven therapeutic activity of the carrier;

stability of the formulation.

One of the simplest aggregation controlling agent is water. Using the proper amount of water unwanted aggregation may be inhibited and the protein is ready to be used according to the invention—it is in "controlled aggregation form".

According to an embodiment of the invention the compounds and compositions may contain as additive a protein aggregation controller or stabilizer and/or solution stabilizing auxiliary additive. Examples for such additives are the following: water, sodium chloride, a buffer, a poly-alcohol such as glycerol, a water-soluble sugar derivative preferably mannitol, sorbitol and/or dulcitol and others.

A further object of the present invention includes the process for the preparation of the new products and the pharmaceutical formulations according to the invention. The process comprises the following steps:

a) dissolving the therapeutically active compound having low aqueous solubility and a substantial binding affinity to plasma proteins ("active substance") in a water-miscible, pharmaceutically acceptable organic solvent, b) combining said solution with the aqueous solution of a plasma protein fraction in controlled aggregation state and optionally c) a further pharmaceutically acceptable auxiliary additive—such as a protein aggregation controller and/or a stabilizer— whereby a true solution is obtained containing the said active substance and the said protein fraction bound together by way of non-covalent bonds;

d) removing the organic solvent preferably by ultrafiltering, dialysing, diafiltrating and/or lyophilising the solution or its concentrate or by combination of these treatments whereby a homogeneous, water-soluble liquid or solid product or pharmaceutical formulation is obtained containing the active substance and the plasma protein fraction;

e) optionally dissolving or diluting the solid or liquid with water whereby a clear, liquid composition is obtained which is suitable for therapeutical administration and f) optionally finishing this product into a parenteral formulation (dosage form) for direct use.

When preparing the new homogenous solid products consisting of the active substances and the proteins bound by way of non-covalent bonds according to the invention it is preferable to use the process comprising the following steps according to the invention:

a) dissolving the therapeutically active compound in a water-miscible, pharmaceutically acceptable organic solvent, b) combining said solution with the aqueous solution of the selected plasma protein fraction in controlled aggregation state whereby a true solution is obtained containing the said active substance and the said protein fraction bound together by way of non-covalent bonds;

c) removing the organic solvent and lyophilising the solution or its concentrate.

The proper way to best eliminate the organic solvent depends on the active substance and on the protein involved. It follows from the nature of the active product (the pair including the active substance and the protein) that the methods applied have to ensure mild conditions. Lyophilisation leads to homogeneous, solid state water-soluble products which on redissolution in water can be administered intraperitonially. It might be advantageous to combine the above steps e.g. to make the process more economical by first preparing a concentrate of the active substance/protein pair and thereafter subjecting said concentrate to lyophilisation. Some of the active substance/protein pairs (e.g. the pair amphothericin B/serum albumin) can be successfully concentrated by way of ultrafiltration or dialysis. Some other pairs (e.g. paclitaxel/HSA) are preferably treated by way of lyophylisation. Some pairs should first be ultrafiltrated and the concentrate obtained should then be subjected to lyophilisation.

It is clear for the expert in the field that on the course of preparation of parenteral pharmaceuticals dilution with water includes dilution with such aqueous solutions which contain further parenterally acceptable additives such as e.g. sodium chloride.

The proper solvent to be used according to the invention to dissolve the active ingredient according to step a) above should have the following properties:
  it should be capable to completely dissolve the active ingredient in its mixture with water and
  its mixture with >50% of water should not denaturalize the protein employed.

Before starting to carry out the process according to the invention using the active ingredient and the protein selected the adequate solvent has to be determined on the basis of the above. It is suitable to use solvents where mixtures containing >50% of water are still capable to dissolve the active ingredient.

Preferred solvents which can be used for step a) of the above process are for example any of the group consisting of an aliphatic $C_{(2-4)}$ monoalcohol or polyalcohol, 70-100% ethanol, dimethyl formamide, methyl formamide.

When preparing the solution containing the protein an aggregation controller and/or solution stabilizer might be present. Such additives include a further or optimal amount of water. They also include agents capable to partially occupy some of the binding sites of the protein to avoid aggregation such as any of the following agents: sodium chloride, a buffer, a poly-alcohol such as glycerol and/or a water-soluble sugar derivative preferably mannitol, sorbitol, dulcitol.

When selecting the optimal conditions in the case of any active ingredient the optimal binding affinities and corresponding aggregation properties have to be determined by preliminary measurements. In the examples below we disclose the full method of such determinations.

According to a preferred embodiment of the invention the compounds used in step a) are paclitaxel and a component of the natural plasma such as serum albumin, an immunoglubulin, glycoprotein, interferon and/or interleukin or recombinants of the same are used. Further embodiments according to the invention include to use as the active substance a water-insoluble cytostatic such as a taxonoide, antibiotic, vitamin, antiinflammatory, analgesic, anticonvulsant, immunosupressant, antiepileptic, anxiolytic, hypnotic, antifungal agent, anticoagulant, lipid peroxidase inhibitor, coronary vasodilator, antiarrythmic agent, cardiotonic, uricosuric, antithrombotic, steroid hormone (progestogen, androgen, testogen) and/or photosensitizer. Preferred active substances that can be used for the process according to the invention include the following: amphotericin B, an adriamicine analogue, apazone, azathioprine, bromazepam, camptothecin, carbamazepine, clonazepam, cyclosporine A, diazepam, dicumarol, digitoxine, dipyridamole, disopyramide, flunitrazepam, gemfibrozil, ketochlorin, ketoconazole, miconazole, niflumic acid, oxazepam, phenobarbital, phenytoin, progesterone, propofol, ritonavir, sulfinpyrazone, suprofene, tacrolimus, tamoxifen, taxonoid, testosterone, tirilazad, trioxsalen, valproic acid and/or warfarin.

A preferred embodiment of the invention consists in the preparation of a homogeneous, solid, water-soluble product consisting of paclitaxel and human serum albumin where the active ingredient and the plasma protein fraction can be in a non-covalent binding. A further preferred embodiment of the invention consists in the preparation of a homogeneous, solid, water-soluble product consisting of a taxonoide of the general formula I and a plasma protein fraction where the active ingredient and the plasma protein fraction are in a non-covalent binding.

It is clear from the above explanations that the present invention is not limited to any of the active substances nor to any of the proteins enlisted above.

A further object of the invention comprises the method of use of the products and formulations according to the invention for treatment of human or veterinary patients. The method consists in administering to a patient in need of a treatment with the active ingredient an effective dose of the composition according to or prepared according to the invention. The doses that have to be applied depend on the active ingredient as well as on the protein used. Doses can be administered to ensure at least the same blood levels which are known to be effective when the specific known active substances are used via other administration routes.

There is provided a preferred method of parenteral treatment of human or veterinary patients with a water-insoluble therapeutically active substance having substantial affinity for binding to plasma protein by way of parenterally administering to a patient in need of a treatment with said active substance an effective dose of the following products preferably using the following dose ranges respectively (calculated on the active substance):
paclitaxel/albumin 70-280 mg/treatment; propofol/albumin 6-10 mg/kG/hour; camptothecin/albumin, gemfibrozil/albumin, cyclosporin A/albumin 3-5 mg/kG/day; amphothericin B/albumin up to 1.5 mg/kG/day, whereby the same dose ranges are used for compounds containing the recombinant proteins respectively.

The compounds, compositions and methods of the invention present advantages including the following:
  it becomes possible to avoid the use of biologically incompatible vehicles, to diminish or totally avoid dose limiting side effects, related to such components like toxic solvents, surface-active agents, emulsifiers and the like
  the use of plasma protein fractions as drug vehicles presents no additional toxic effects—to the contrary they may improve the tolerance of the patients e.g. in the case of chemotherapy
  in desired cases the applied dose can be increased as compared with the drugs now marketed presenting thus a possibility to improve the overall outcome of therapy.

The present invention is illustrated in a more detailed manner in the following examples without the intention of limitation:

Examples

I. Preparative Methods, Assays

The following methods were applied to determine the binding of a particular active ingredient (substance) to a protein:

a) Ultrafiltration

A 1 ml sample of the clear solution formed by admixture of the aqueous solution containing the protein in controlled aggregation state and the solution of the active ingredient in an appropriate solvent is filtered through an ultrafiltration membrane (cut off limit >30000 Da) and the active ingredient is determined in the ultrafiltrate fraction. When measuring the active ingredient concentration in the unfiltered solution the total amount (>90%) is recovered in unchanged form.

b) Lyophilisation 1 ml of the above solution is lyophilised. After lyophilization the solid residue is dissolved in about 1.00 ml of distilled water, giving a clear solution. Measuring the active ingredient concentration of this solution no active ingredient is found in the water phase but 100% is recoverable from the protein fraction.

c) Analysis of the Active Ingredient

The assays for the determination of the active ingredient are done by HPLC with detection by UV spectroscopy.

The HPLC analysis can be carried out e.g. on a Waters Millennium (Waters, Mass., USA) HPLC system. Its components are: Waters 616 pump; Waters 600S controller; Waters 717 plus automatic sample injector, with thermostat set to +5° C.; Waters 996 diode array UV/VIS detector. The system is driven and the data acquisition done by Waters Millennium v.2.02.0 run on a Digital P486/166 (Digital Equipments, Irvin, UK) personal computer. The conditions have to be optimised individually for each compound, as exemplified below for several products.

d) Proof of the Chemical Structure

The LC/MS method is used to prove that the chemical structure of the substance recovered from the bound fraction remained unchanged. The LC/MS assays are performed on a Finnigan Navigator (Finnigan, Manchester, UK) single quandrupole LC/MS mass spectrometer using the ES or APCI+ ionisation mode, with a MassLab v.2.0 data acquisition system run on a Digital Venturis FX/166 (Digital Equipments, Irvin, UK) personal computer. The applied conditions have to be optimised individually for each specific substance, based on the references—as exemplified in several of the following examples.

e.) Preparation of Samples

The following is a typical sample preparation method, used to determine the total concentration/amount of a substance from a sample by HPLC and/or LC/MS analysis.

The solid content of lyophilisation vial is reconstituted with water, the solution is mixed with absolute ethanol in a ratio of 1:1 by volume, precipitating the plasma proteins, while the substances dissolved. After a quick centrifugation, the solution is suitable for HPLC or LC/MS analysis. In LC/MS it is analysed by direct sample introduction or through HPLC by way of separating the components from one another. Both methods give valuable information about the chemical structure of the parent compound and/or the possible degradation products, as exemplified in more detailed manner for several products below The chromatographic and mass spectroscopic data from the HPLC and LC/MS studies can confirm the chemical equivalence between the known biologically active substance used as the starting material and the compound recovered after having been bound to a protein fraction according to the invention.

f.) Materials Used

All active substances used were of USP XXIII quality. The following plasma protein fractions were used in the experiments: (*=Ph. Eur. quality)

| | |
|---|---|
| Human Albumin 20% sol.* | HUMAN Rt., Gödöllö, Hungary |
| Recombumin ™ 25% | DELTA Biot. Ltd, Nottingham, UK |
| Humanalbumin 20% * | Biotest Ph., Dreieich, Germany |
| Albumeon USP | Centeon Bio-Services, Little Rock, AR, USA |
| Human Albumin 20% Behring* | Centeon Ph. GmbH, Wien, Austria |
| Human Gamma Globulin 16%* | HUMAN Rt. Gödöllö, Hungary |

II. Preparation and Chemical or Physical Assays

In the following examples the plasma protein:substrate binding ratios are in the average range falling between 1:0.1-100. The substance:HSA binding ratios were calculated based on the assumption for HSA mw=66500, and human gamma globulin mw=150000 [see 11 Science, VOL. 244. P. 1195-1198, 1989; Vox Sang, 70: p. 203-209, 1996]

Example II.1

The 20% ($3.08 \times 10^{-3}$ M) solution of human serum albumin in controlled aggregation state and the 1 mg/ml ($1.17 \times 10^{-3}$ M) solution of paclitaxel in absolute ethanol were admixed in 4:1 ratio and stirred so as to obtain a clear solution.

The solution is lyophilised; the solid residue is redissolved in sufficient water to ensure a clear solution having the concentration of 20% for human serum albumin. The binding is determined from UF filtrate and retentate fractions, showing 99% binding of paclitaxel to human serum albumin. This represents a 1:0.1 ratio of human serum albumin:paclitaxel.

Example II.2

The 4.44% ($6.67*10^{-4}$ M) solution of human serum albumin in controlled aggregation state and the 2.0 mg/ml ($2.34*10^{-3}$ M) solution of paclitaxel (mw 853.92) in absolute ethanol are mixed in a 9:1 ratio and stirred until a clear solution is obtained. The solution is further treated as described in Example II.1.

The binding is determined from UF filtrate and retentate fractions, showing 99% binding of paclitaxel to human serum albumin. This represents a 1:0.39 ratio of human serum albumin:paclitaxel.

Example II.3

The 4.44% ($6.67*10^{-4}$ M) solution of recombinant human serum albumin in controlled aggregation state and the 2.0 mg/ml ($1.40*10^{-3}$ M) solution of paclitaxel in absolute ethanol are mixed in 9:1 ratio and stirred obtaining a clear solution.

The solution was lyophilised; the solid residue was redissolved in sufficient water to ensure a clear solution having the concentration of 20% for recombinant human serum albumin. The binding is determined from UF filtrate and retentate fractions, showing 99% binding of paclitaxel to recombinant human serum albumin. This represents a 1:0.24 ratio of recombinant human serum albumin:paclitaxel.

Example II.4

A 2.25% ($1.5*10^{-4}$ M) solution of human gamma globulin in controlled aggregation state and a 0.1 mg/ml ($1.171*10^{-4}$ M) solution of paclitaxel in absolute ethanol are admixed in a 9:1 ratio and stirred until a clear solution is obtained. The solution is lyophilised; the solid residue is redissolved in enough water to ensure a concentration of 16% for human gamma globulin, obtaining a clear solution.

The binding is determined from UF filtrate and retentate fractions, showing 98% binding of paclitaxel to human gamma globulin. This represents a 1:0.71 ratio of human gamma globulin:paclitaxel.

In the above Examples II.1 through II.3 the quantity of paclitaxel was measured by HPLC following the method:

| column | MN Nucleosil $C_{18}$ 5 μm 250 × 2 mm |
|---|---|
| mobile phase | acetonitrile:water = 73:27 |
| flow rate | 0.30 ml/min |
| temperature | ambient |
| detection | at 273 nm |
| typical retention time | 5.9 min; k' = 2.93 |

Figure 6A:
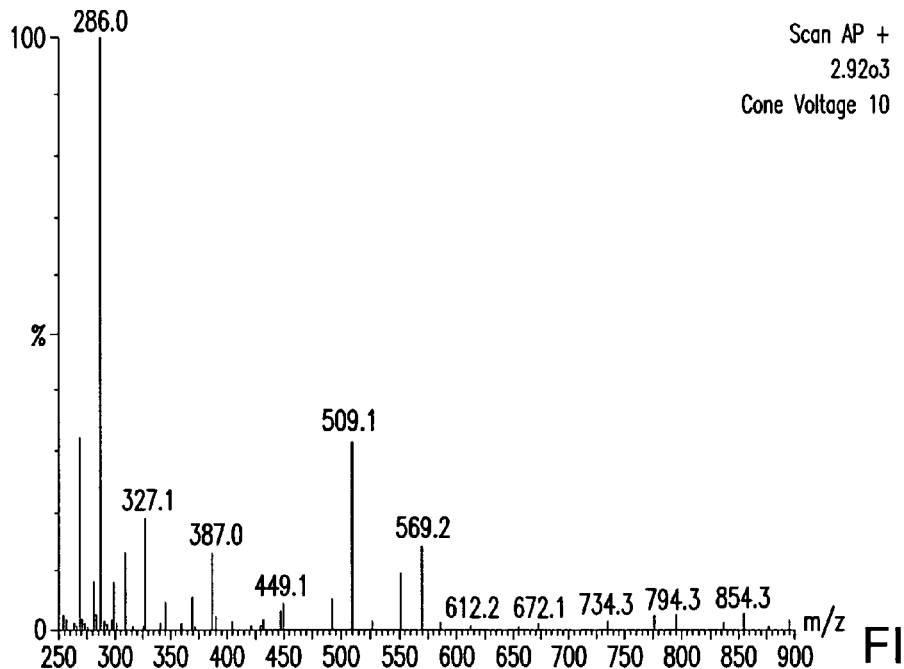
FIG. 6A shows the mass spectrum of the standard.
Figure 6B:
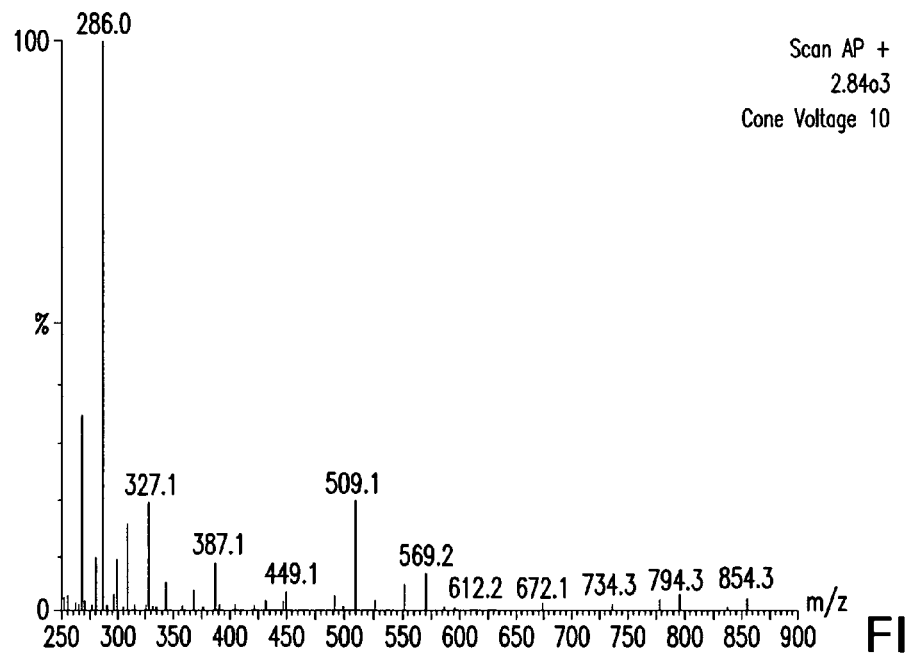
FIG. 6B shows the curve of the re-dissolved sample.
Figure 6C:
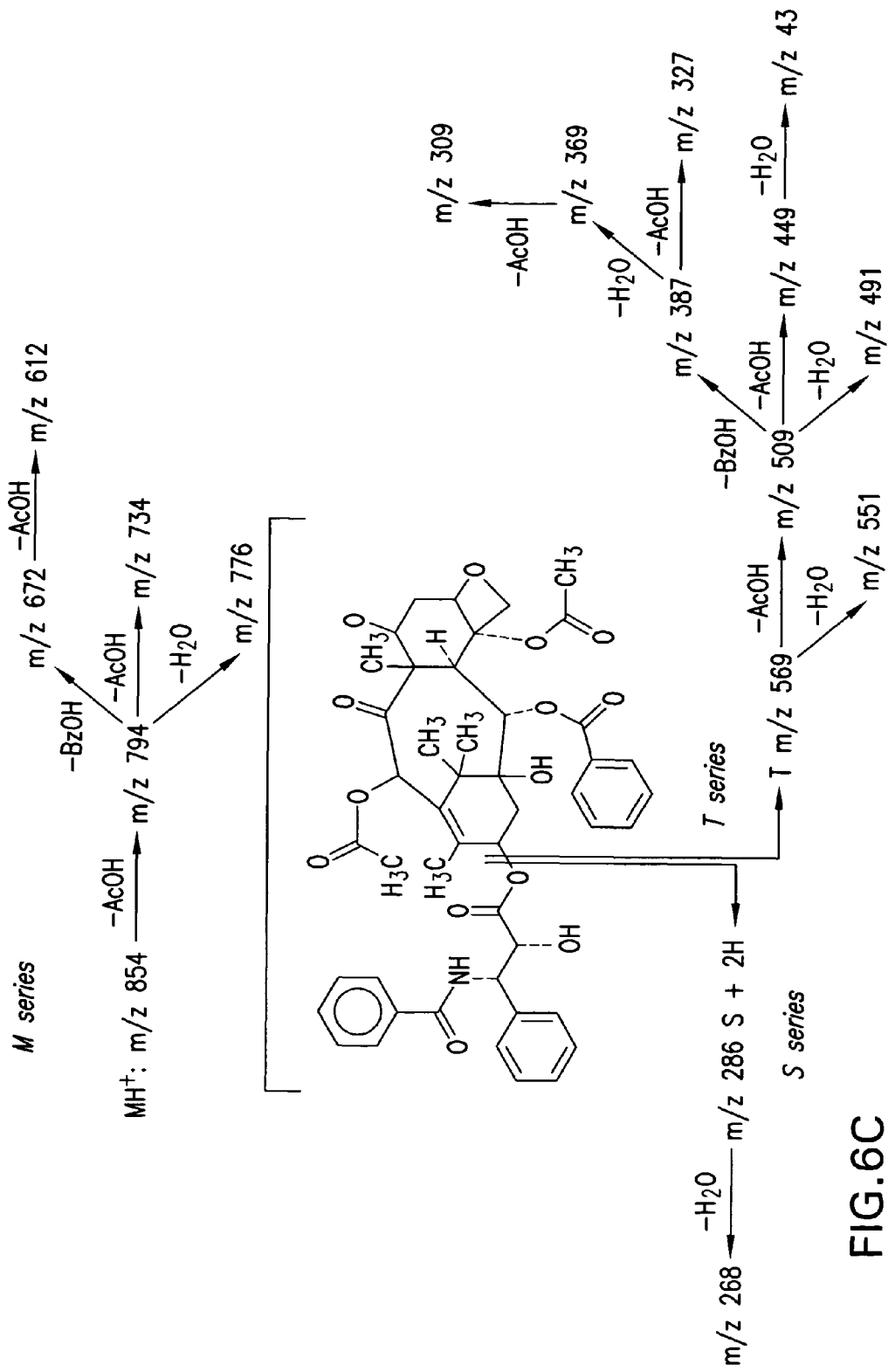
FIG. 6C shows the curve of the fragmentation of paclitaxel.

The substance was determined and found unchanged by LC/MS [see Rapid Communications in Mass Spectrometry VOL. 11: p 1025-1032, 1997. and Rapid Communications in Mass Spectrometry, VOL. 9, p. 495-502, 1995.]. The comparative results are shown in FIG. 6: FIG. 6A shows the mass spectrum of the standard, FIG. 6B shows the curve of the re-dissolved sample. FIG. 6C shows the fragmentation of paclitaxel.

LC/MS parameters: ionisation: APCI+interface; nitrogen gas flow rate: 300 l/h; solvent: acetonitrile:buffer=60:40, where the buffer is 10 mM ammonium formate pH 5.0 adjusted with 10% formic acid; flow rate: 0.300 ml/min.

Assay for the Determination of Paclitaxel:

A C-18 reverse phase HPLC method was applied for the quantitative determination of paclitaxel from different solutions of Examples II.1 through II.27. The samples were injected into the HPLC system in ≥50% ethanol solution, preventing any precipitation of the substance.

Binding

The binding of the substance to plasma proteins is determined after 15 minutes equilibration at 8±2 C.°.

The distribution of the substance is measurable after ultrafiltration through an appropriate membrane (cut-off must be >than the Mw= of the protein), determining the substance concentration in the ultrafiltrate fraction (representing the unbound) and in the prefiltered solution, releasing the bound part upon denaturation of the protein (representing the total). To denature the protein and release the bound fraction pre-cooled (8±2° C.) absolute ethanol is used in 1:1 ratio. The exact concentration values and amounts are calculated in consideration of the dilution factor.

Examples II.5 to II.21

The solution of human serum albumin in the concentration range of 20% ($3.08 \times 10^{-3}$ M) to 0.02% ($3.08 \times 10^{-6}$ M) is combined with the solution of paclitaxel in absolute ethanol in the concentration range from 20 mg/ml ($2.34 \times 10^{-2}$ M) to 0.01 mg/ml ($1.17 \times 10^{-5}$ M) obtaining always clear solutions. Details are presented in Table I. All measurements are performed three times and the calculated results are averaged.

TABLE I

| Example | $[T]_T$ (mM) | [HAS] (mM) | $n(T_B)/n$ (HAS) | $n(T_B)/n/T_T \times 100\%$ |
|---|---|---|---|---|
| II.5 | 0.2342 | 2.410 | 0.093 | 97.4 |
| II.6 | 0.2342 | 1.205 | 0.177 | 93.2 |
| II.7 | 0.2342 | 0.602 | 0.346 | 91.0 |
| II.8 | 0.2342 | 0.301 | 0.648 | 85.2 |
| II.9 | 0.2342 | 0.121 | 1.545 | 81.2 |
| II.10 | 0.2342 | 0.0602 | 3.125 | 82.1 |
| II.11 | 0.2342 | 0.0241 | 5.662 | 59.5 |
| II.12 | 0.2342 | 0.0121 | 4.948 | 26.0 |
| II.13 | 0.2342 | 0.00602 | 5.823 | 15.3 |
| II.14 | 0.2342 | 0.00241 | 10.419 | 11.0 |
| II.15 | 0.2342 | 0.00121 | 14.367 | 7.6 |
| II.16 | 0.2342 | 0.000602 | 12.370 | 3.3 |
| II.17 | 4.6843 | 0.121 | 4.135 | 10.9 |
| II.18 | 2.3421 | 0.121 | 8.401 | 44.2 |
| II.19 | 1.1711 | 0.121 | 4.585 | 48.2 |
| II.20 | 0.4648 | 0.121 | 2.864 | 75.3 |
| II.21 | 0.1171 | 0.121 | 0.765 | 80.4 |

Legend:
$[T]_T$ total paclitaxel concentration after addition to human serum albumin
[HSA] concentration of human serum albumin
$n(T_B)/n(HSA)$ number of moles of paclitaxel bound per mole of human serum albumin
$n(T_B)/n/T_T \times 100\%$ percentage of bound paclitaxel.

Figure 9:
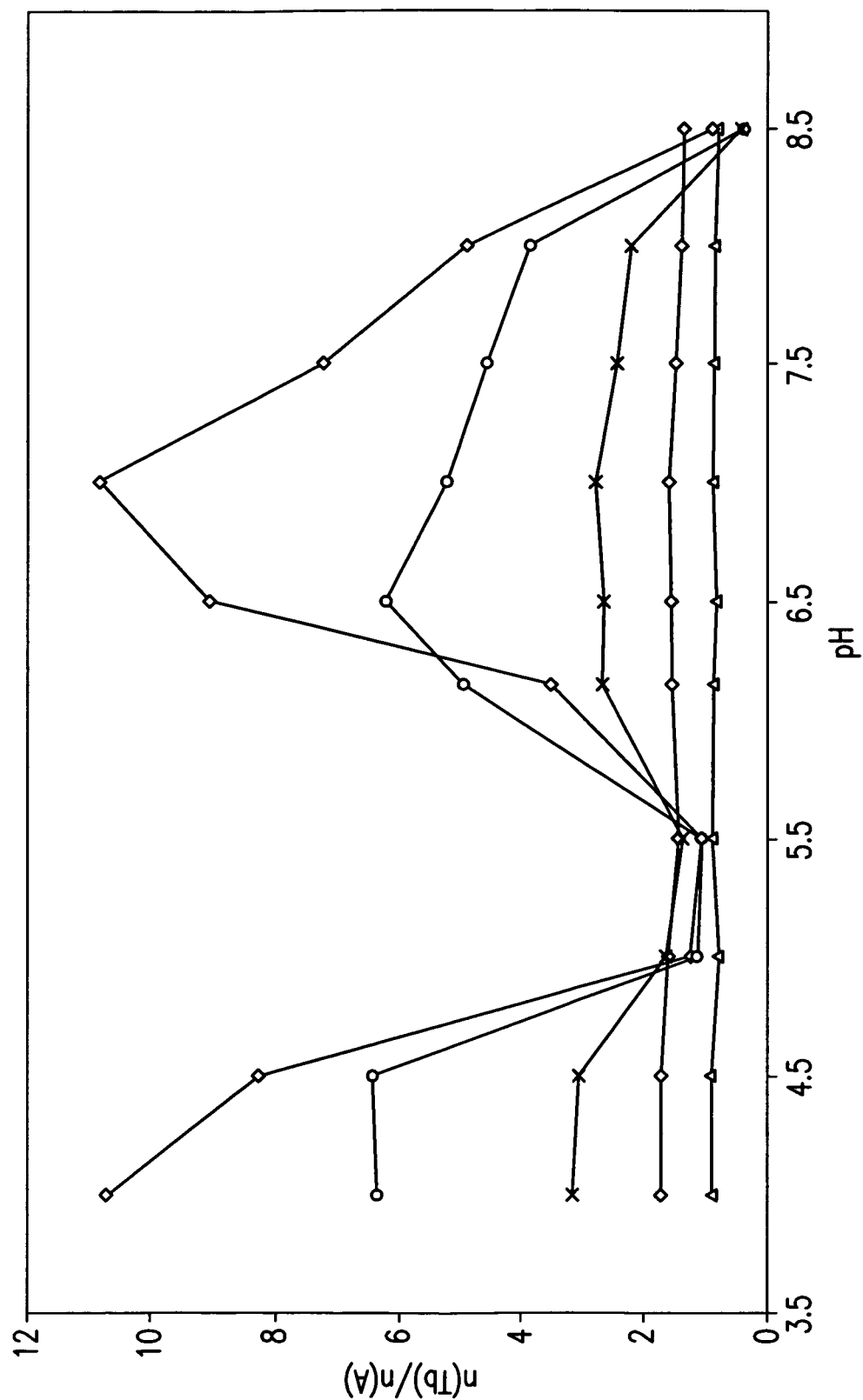
FIG. 9 shows the variation of paclitaxel binding to HSA (with 0.8% HSA, 10% ethanol, 0.1 to 2.0 mg/ml paclitaxel) as a function of pH at values of pH 4.0 to 8.5.

Variation of paclitaxel concentration (with 0.08% HSA, 10% ethanol, 0.002 mg/ml paclitaxel) is shown on FIG. 7; variation of albumin concentration (with 0.004 16.0% HSA, 20% ethanol, 0.2 mg/ml paclitaxel) is shown on FIG. 8. variation of paclitaxel binding to HSA (with 0.8% HSA, 10% ethanol, 0.1 to 2.0 mg/ml paclitaxel) as a function of pH at values of pH 4.0 to 8.5 is shown on FIG. 9. The signs on the graph correspond to the following examples:

| Example | II.18 | -♦-♦- |
|---|---|---|
| Example | II.19 | -O-O- |
| Example | II.20 | -X-X- |
| Example | II.15 | -◇-◇- |
| Example | II.21 | -A-A- |

Example II.22

Similar methods as above in Examples II.2 to II.21 are used with animal serum albumin, immunoglobulin, glycoproteides, interferons and interleukines.

Example II.23

Treatment of commercially available human serum albumin or recombinant human serum albumin (in the following albumin) to achieve the controlled aggregation state with the best binding conditions of the molecule include removal of stabilisers, such as sodium caprylate, N-acetyl-D,L-tryptophan and other ionic components and salts.

a.) Ultrafiltration Method

Adjust the pH of the solution containing 10% albumin to 3.0 with hydrochloric acid and dilute to 5% protein content with bi-distilled water. Concentrate the solution to 10% for protein content using ultrafiltration (membrane cut off limit 30000 kD).

Dilute the solution back to 5% protein content with 1.0 mM hydrochloric acid. Concentrate the solution to 10% protein content using ultrafiltration (membrane cut off limit 30000 kD).

Repeat the procedure 12×, then adjust the pH to 6.9 with a 2.0 M aqueous sodium hydroxide solution and dilute the solution to 5% concentration for protein content with bi-distilled water. Concentrate the solution to 10% for protein content using ultrafiltration (membrane cut off limit 30000 kD) again Dilute the solution back to 5% for protein content with bi-distilled water. Concentrate the solution to 10% for protein content using ultrafiltration (membrane cut off limit 30000 kD). Repeat the procedure 10×, obtaining a pure protein fraction, sufficiently free from other excipients. By that time, the conductivity of the ultrafiltrate is close to that of the bi-distilled water used for dilution. This protein is adequate for use to bind e.g. paclitaxel or cyclosporin.

b.) Instead of ultrafiltration the use of dialysis gives similar results. The treatment requires about 48 hours.

Example II.24

The 0.8% ($1.203*10^{-4}$ M) solution of HSA and the 4.0 mg/ml ($4.33*10^{-3}$ M) solution of amphotericin B (mw=924.09) in DMF were mixed in a 9:1 ratio and stirred obtaining a clear solution.

The solution was lyophilised; the solid residue was redissolved using enough water to ensure that the concentration was 20% for HSA, obtaining a clear solution. The binding was determined from UF filtrate and retentate fractions, showing 99.7% binding of amphotericin B to HSA. This represents a 1:4 ratio for HSA:amphotericin B.

Example II.25

The 0.8% ($1.203*10^{-4}$ M) solution of recombinant human serum albumin and the 40.0 mg/ml ($4.33*10^{-2}$ M) solution of amphotericin B in DMF+HCl are mixed in a 9:1 ratio and stirred obtaining a clear solution.

The solution is lyophilised; the solid residue is redissolved in sufficient water to make the final concentration 20% for recombinant HSA, obtaining a clear solution. The binding is determined from the UF filtrate and retentate fractions, showing 99.5% binding of amphotericin B to HSA. This represents a 1:40 ratio for recombinant HSA:amphotericin B.

Amphotericin B is measured by HPLC following the method below:

| | |
|---|---|
| column | MN Nucleosil $C_{18}$ 5 μm 250 × 2 mm |
| mobile phase | acetonitrile:buffer = 1:1 |
| | (buffer: 0.2% formic acid pH adjusted to 4.0 with triethylamine) |
| flow rate | 0.30 ml/min |
| temperature | ambient |
| detection | at 365 nm |
| typical retention time | 5.3 min, k' = 1.41 |

Figure 2A:
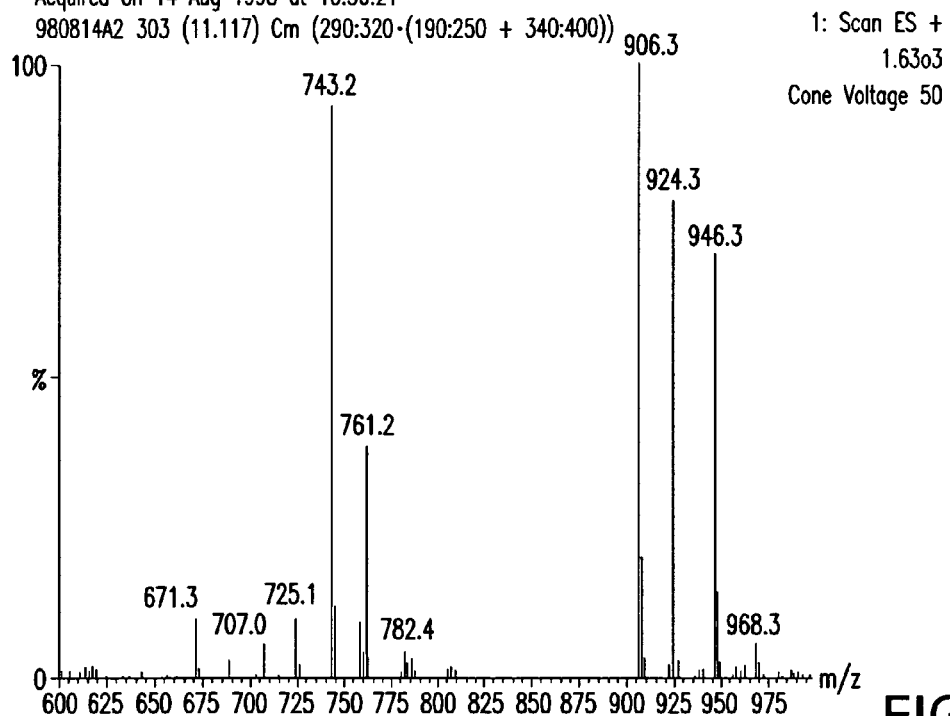
FIG. 2A shows the mass spectrum of the standard.
Figure 2B:
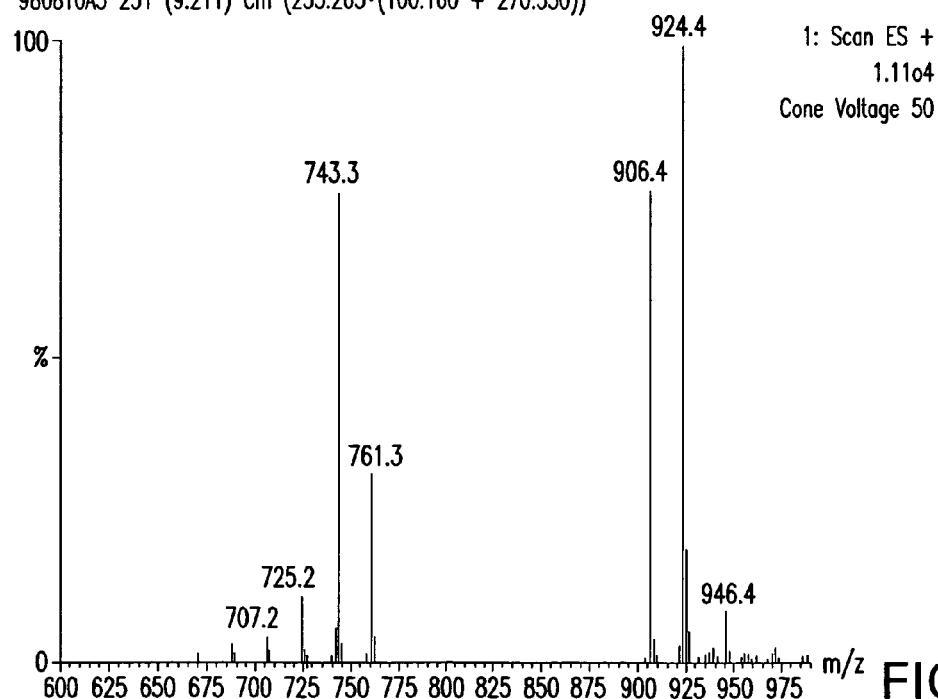
FIG. 2B shows the curve of the re-dissolved sample.
Figure 2C:
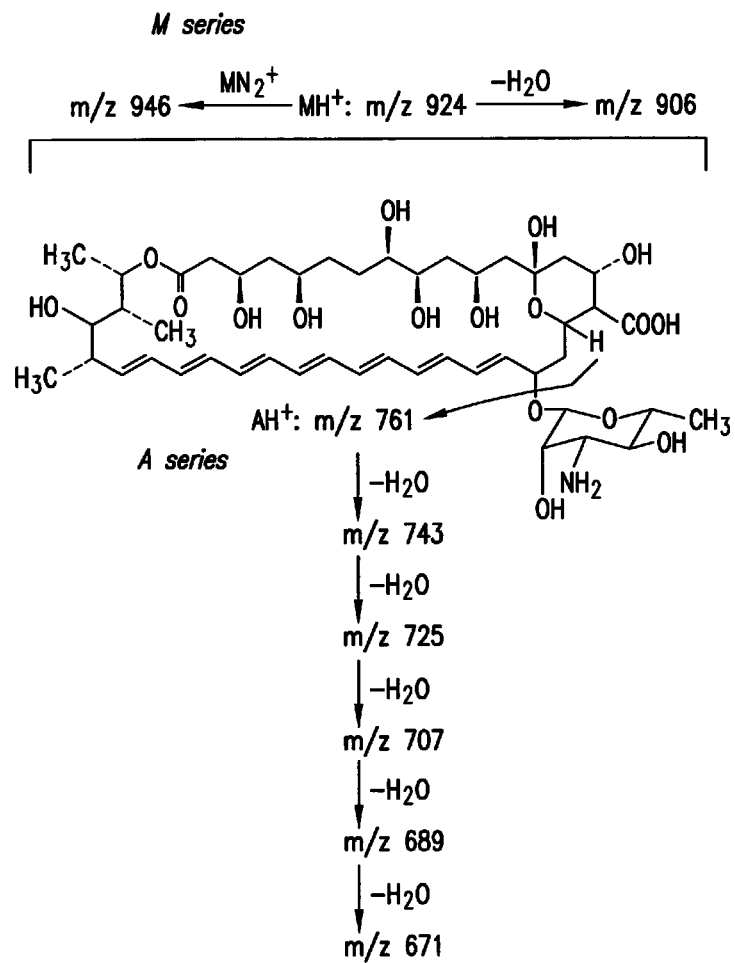
FIG. 2C shows the fragmentation of amphotericin B.

The substance is determined and found unchanged using LC/MS. The comparative results are shown in FIG. 2: FIG. 2A shows the mass spectrum of the standard, FIG. 2B shows the curve of the re-dissolved sample. FIG. 2C shows the fragmentation of amphotericin B.

LC/MS parameters: ionisation: ESI+interface;

nitrogen gas flow rate: 300 l/h; solvent: 20 mM ammonium formate pH 4.0 adjusted with 10% formic acid; flow rate: 0.300 ml/min.

Example II.26

The 0.4% ($6.015*10^{-5}$ M) solution of HSA in controlled aggregation state and the. 0.14 mg/ml ($4.02*10^{-4}$ M) solution of camptothecin (mw=348.36) in abs. ethanol were admixed in a 4:1 ratio and stirred to obtain a clear solution. The solution was lyophilised; the solid residue was redissolved in enough water to ensure that the final concentration was 20% for HSA, thereby obtaining a clear solution. The binding was determined from the UF filtrate and retentate fractions, showing 98% binding of camptothecin to HSA. This represents a 1:5.34 ratio of HSA:camptothecin.

Example II.27

The 0.4% ($6.015*10^{-5}$ M) solution of recombinant HSA in controlled aggregation state and the 0.14 mg/ml ($4.02*10^{-1}$ M) solution of camptothecin in abs. ethanol were mixed in 4:1 ratio and stirred obtaining a clear solution.

The solution was lyophilised; the solid residue was redissolved in that much water as the final concentration was 20% for recombinant HSA, obtaining a clear solution. The binding was determined from UF filtrate and retentate fractions, showing 98% binding of camptothecin to HSA. This represents a 1:5.34 ratio of recombinant HSA:camtothecin.

We measured the camptothecin by HPLC as follows:

| | |
|---|---|
| column | MN Nucleosil $C_{18}$ 5 μm 250 × 2 mm |
| mobile phase | acetonitrile:buffer = 33.67 |
| flow rate | 0.33 ml/min |
| temperature | ambient |
| detection | at 356 nm. |
| typical retention time | 6.9 min k' = 2.45 |

The substance was determined and found unchanged by LC/MS [Cancer Research, VOL. 56: p.3689-3694, 1996.]

Example II.29

The 4.0% ($6.015*10^{-4}$ M) solution of HSA in controlled aggregation state and the 8.0 mg/ml ($3.39*10^{-2}$ M) solution of carbamazepin (mw 236.27) in abs. ethanol were admixed in 19:1 ratio and stirred obtaining a clear solution. The solution was lyophilised; the solid residue was redissolved in a sufficient amount of water to make the final concentration 20% for HSA, obtaining a clear solution. The binding was determined from UF filtrate and retentate fractions, showing 98% binding of carbamazepin to HSA. This represents a 1:2.8 ratio of HSA:carbamazepine.

The carbamazepin was measured by HPLC following the method below:

| | |
|---|---|
| column | MN Nucleosil $C_{18}$ 5 μm 250 × 2 mm |
| mobile phase | acetonitrile:buffer = 1:1 |
| | (buffer: 0.2% formic acid pH adjusted to 7.0 with triethylamine) |
| flow rate | 0.25 ml/min |
| temperature | ambient |
| detection | at 285 nm |
| typical retention time | 5.3 min k' = 1.12 |

Figure 3A:
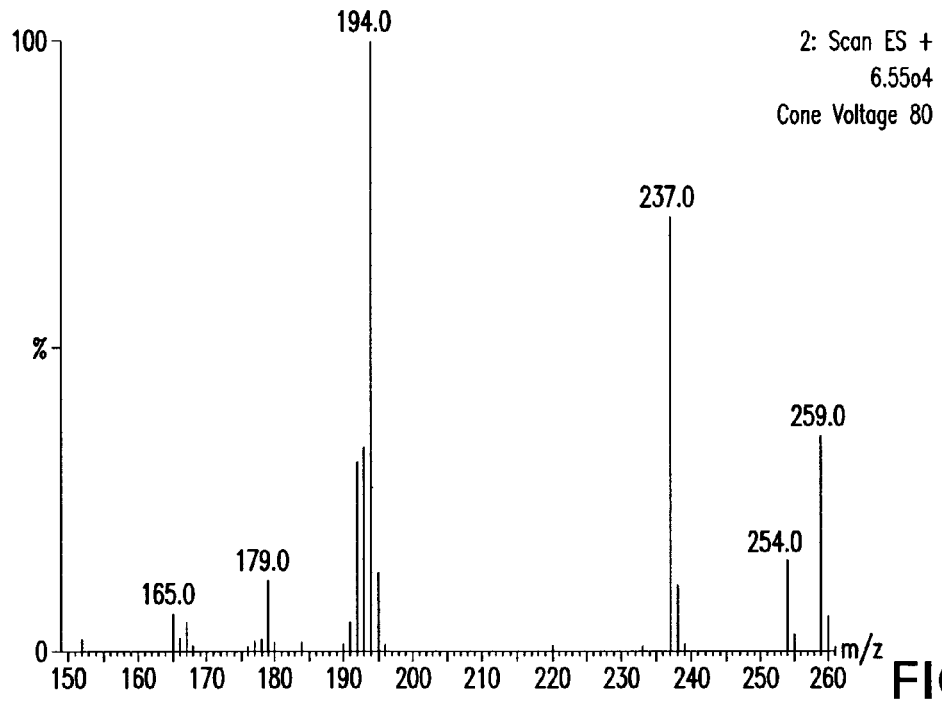
FIG. 3A shows the mass spectrum of the standard.
Figure 3B:
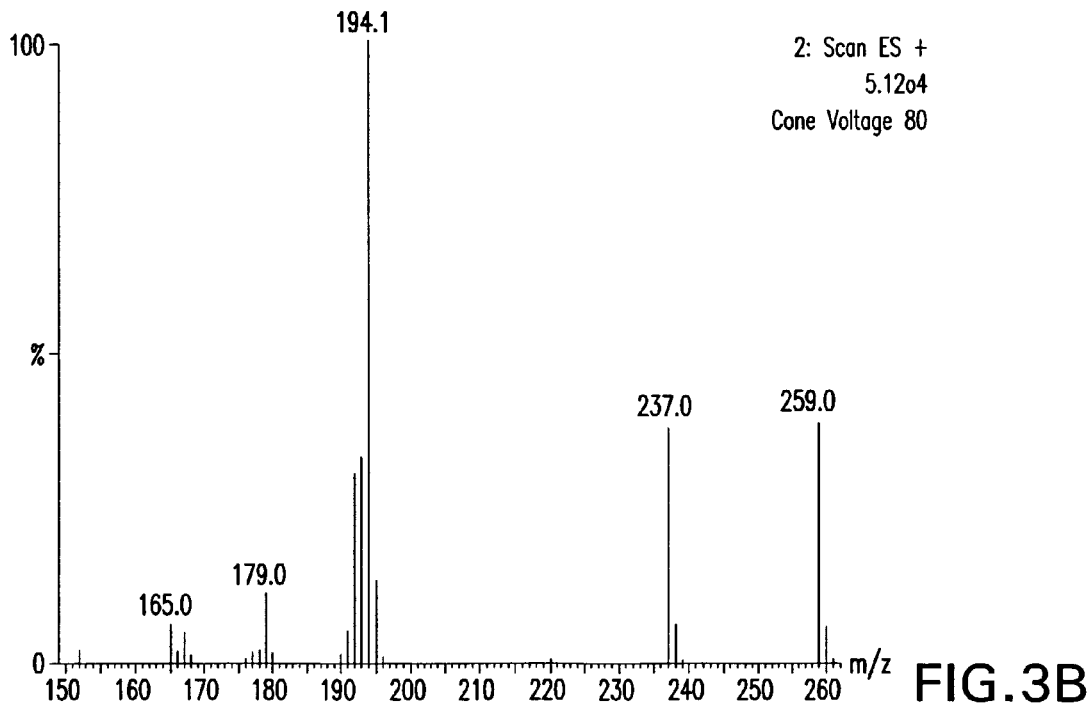
FIG. 3B shows the curve of the re-dissolved sample.
Figure 3C:
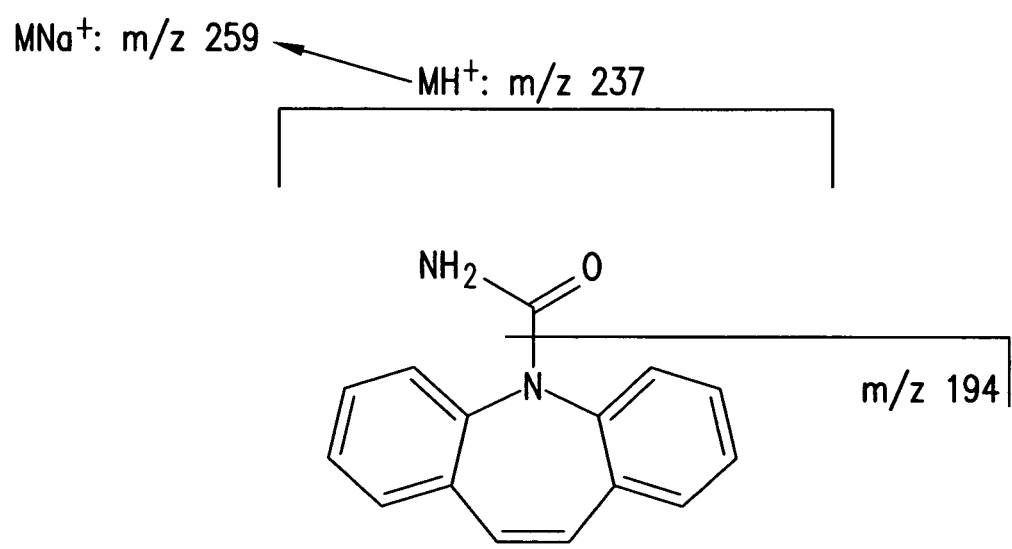
FIG. 3C shows the fragmentation of carbamazepin.

The substance was determined and found unchanged by LC/MS [Eur. J. Clin. Chem Clin. Biochem, VOL. 35(10): p. 755-759, 1997]. The comparative results are shown in FIG. 3: FIG. 3A shows the mass spectrum of the standard, FIG. 3B shows the curve of the re-dissolved sample. FIG. 3C shows the fragmentation of carbamazepin.

LC/MS parameters: ionisation: ESI+interface; nitrogen gas flow rate: 300 l/h; solvent: 2 mM ammonium formate; flow rate: 0.250 ml/min.

Example II.30

The 4.0% ($6.015*10^{-4}$ M) solution of HSA in controlled aggregation state and the 1.0 mg/ml ($8.33*10^{-4}$ M) solution of cyclosporine A (mw 1202.63) in absolute ethanol were mixed in 9:1 ratio and stirred obtaining a clear solution.

The solution was lyophilised; the solid residue was redissolved in a sufficient amount of water to make the final concentration 20% for HSA, obtaining a clear solution. The binding was determined from UF filtrate and retentate fractions, showing 97% binding of cyclosporine A to HSA. This represents a 1:0.14 ratio for HSA:cyclosporine A.

Example II.31

The 2.0% ($3.008*10^{-4}$ M) solution of recombinant HSA in controlled aggregation state and the 1.0 mg/ml ($8.33*10^{-4}$ M) solution of cyclosporine A in absolute ethanol were mixed in 9:1 ratio and stirred obtaining a clear solution.

The solution was lyophilised; the solid residue was redissolved in a sufficient amount of water to make the final concentration 20% for recombinant HSA, obtaining a clear solution. The binding was determined from UF filtrate and retentate fractions, showing 98% binding of cyclosporine A to recombinant HSA. This represents a 1:0.29 ratio for recombinant HSA:cyclosporine A.

Example II.32

The 2.25% ($1.50*10^{-4}$ M) solution of human gamma globulin and the 1.0 mg/ml ($8.33*10^{-4}$ M) solution of cyclosporine A in absolute ethanol were mixed in a 9:1 ratio and stirred obtaining a clear solution.

The solution is lyophilised; the solid residue is redissolved in enough water to give a concentration of 16.% for human gamma globulin, thereby obtaining a clear solution. The binding is determined from the UF filtrate and retentate fractions, showing 98% binding of cyclosporine A to human gamma globulin. This represents a 1:0.56 ratio for human gamma globulin:cyclosporine A.

The cyclosporine A was measured by HPLC following the method below:

| column | MN Nucleosil $C_{18}$ 5 μm 250 × 2 mm |
| --- | --- |
| mobile phase | acetonitrile:water:methanol:phosphoric acid = 700:260:40:0.05 |
| flow rate | 0.350 ml/min |
| temperature | 80° C. thermostat |
| detection | at 205 nm |
| typical retention time | 7.5 min k' = 2.95 |

Figure 4A:
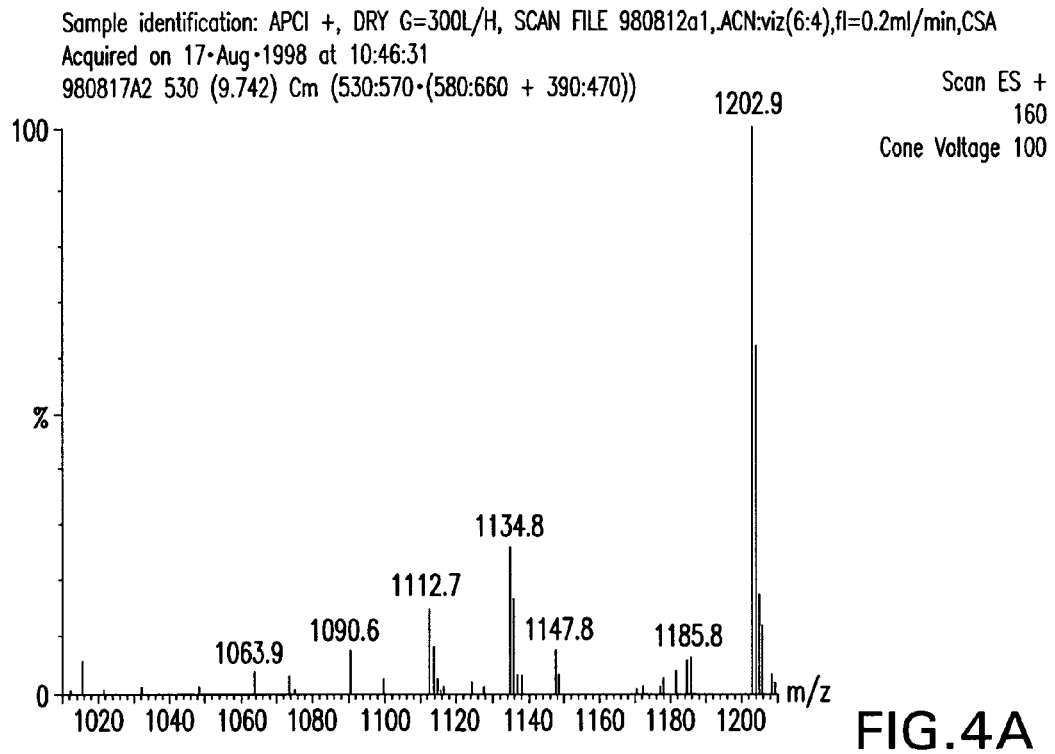
FIG. 4A shows the mass spectrum of the standard.
Figure 4B:
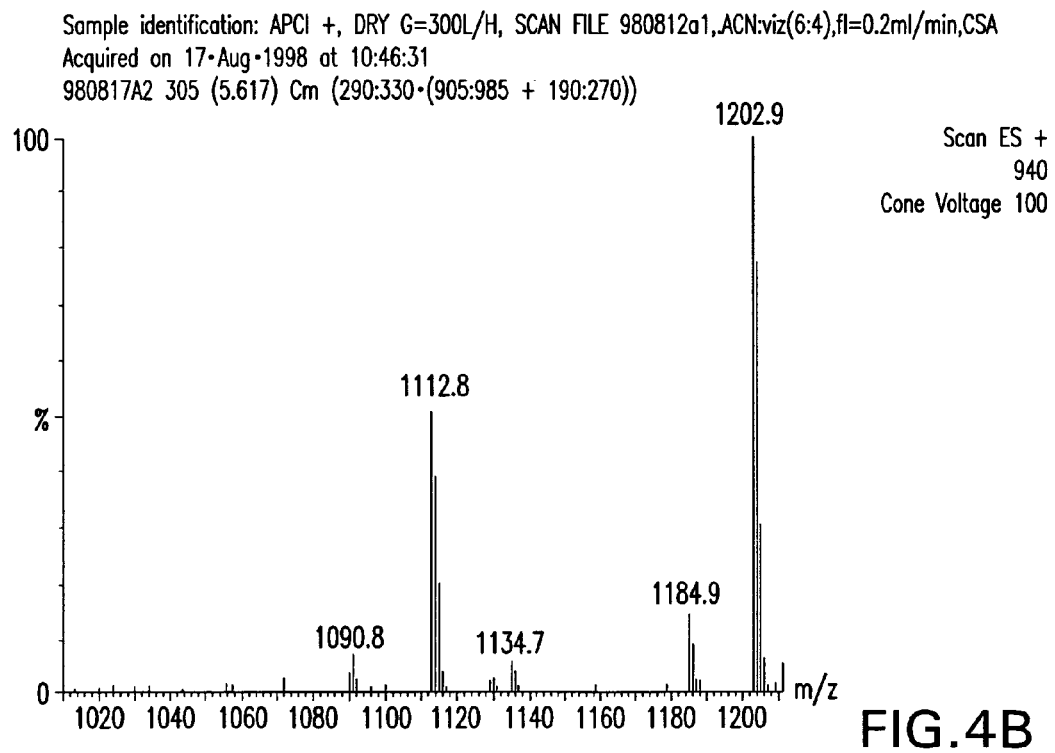
FIG. 4B shows the curve of the re-dissolved sample.
Figure 4C:
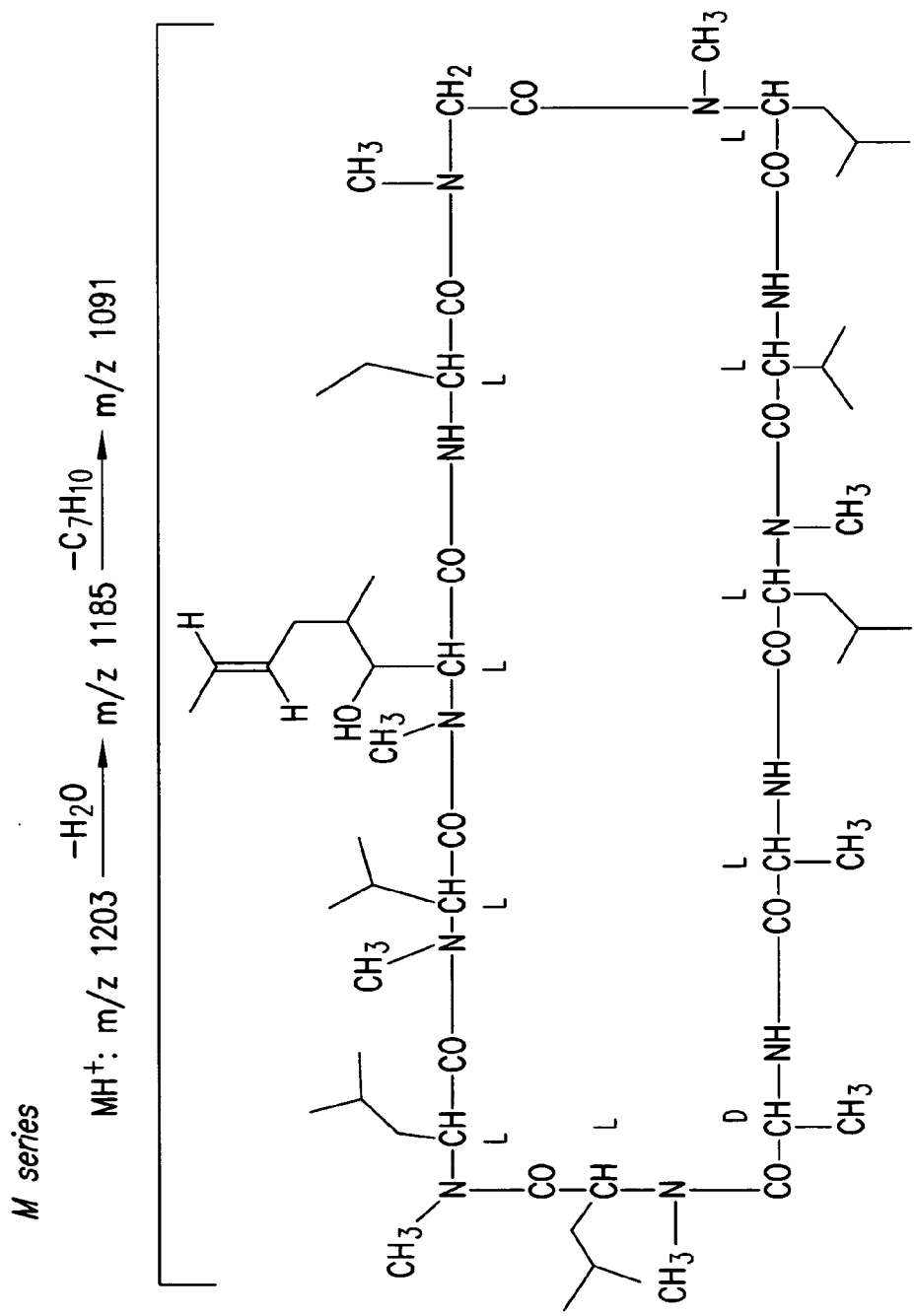
FIG. 4C shows the fragmentation of cyclosporine A.

The substance was determined and found—unchanged by LC/MS [1], as the results show. The comparative results are shown in FIG. 4: FIG. 4A shows the mass spectrum of the standard, FIG. 4B shows the curve of the re-dissolved sample. FIG. 4C shows the fragmentation of cyclosporine A.

LC/MS parameters: ionisation: ESI+interface, nitrogen gas flow rate: 300 l/h; solvent: acetonitrile/water=60/40; solvent flow rate: 0.350 ml/min.

Example II.33

The 0.4% ($6.015*10^{-5}$ M) solution of HSA and the 2.0 mg/ml ($1.12*10^{-2}$ M) solution of propofol (mw178.27) in absolute ethanol were mixed in 9:1 ratio and stirred obtaining a clear solution.

The solution was lyophilised; the solid residue was redissolved in a sufficient amount of water to make the final concentration 20% for HSA, obtaining a clear solution. The binding was determined from UF filtrate and retentate fractions, showing 99% binding of propofol to HSA. This represents a 1:18.3 ratio of HSA:propofol.

Example II.34

The 0.4% ($6.015*10^{-5}$ M) solution of recombinant HSA and the 2.0 mg/ml ($1.12*10^{-2}$ M) solution of propofol in absolute ethanol were mixed in 9:1 ratio and stirred obtaining a clear solution.

The solution is lyophilised; the solid residue was redissolved in a sufficient amount of water to make the final concentration 20% for recombinant HSA, obtaining a clear solution. The binding was determined from UF filtrate and retentate fractions, showing 99% binding of propofol to recombinant HSA. This represents a 1:18.3 ratio of recombinant HSA:propofol.

Propofol was measured by HPLC as follows:

| column | MN Nucleosil $C_{18}$ 5 μm 250 × 2 mm |
| --- | --- |
| mobile phase | acetonitrile:water = 73:27 |
| flow rate | 0.30 ml/min |
| temperature | ambient |
| detection | at 273 nm |
| typical retention time | 6.1 min k' = 1.77 |

Figure 5A:
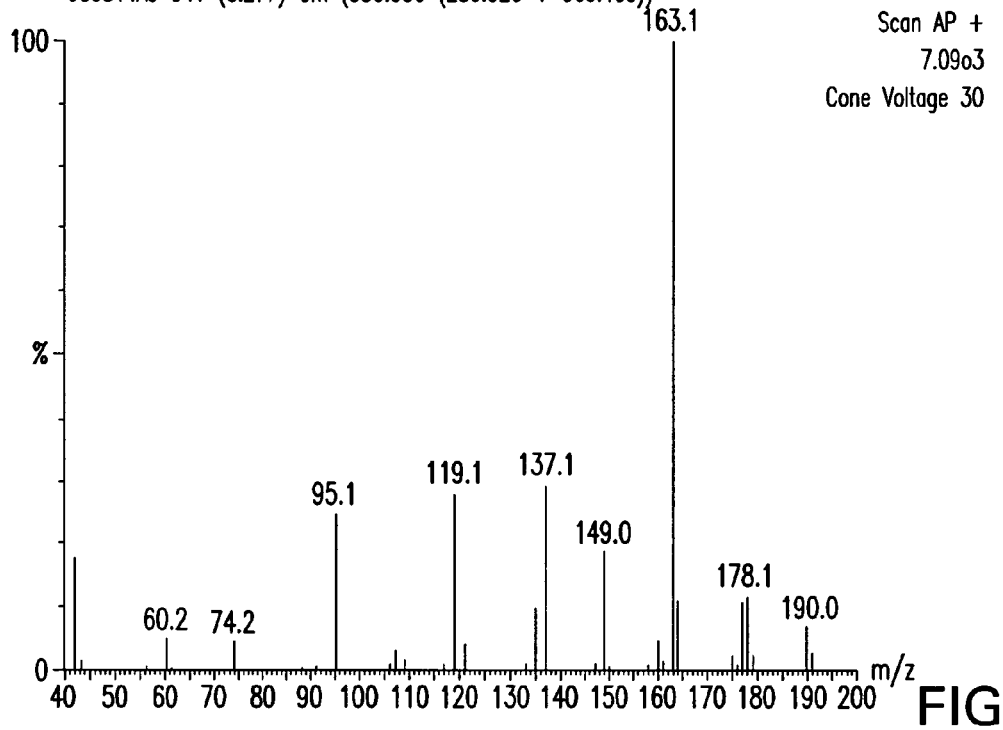
FIG. 5A shows the mass spectrum of the standard.
Figure 5B:
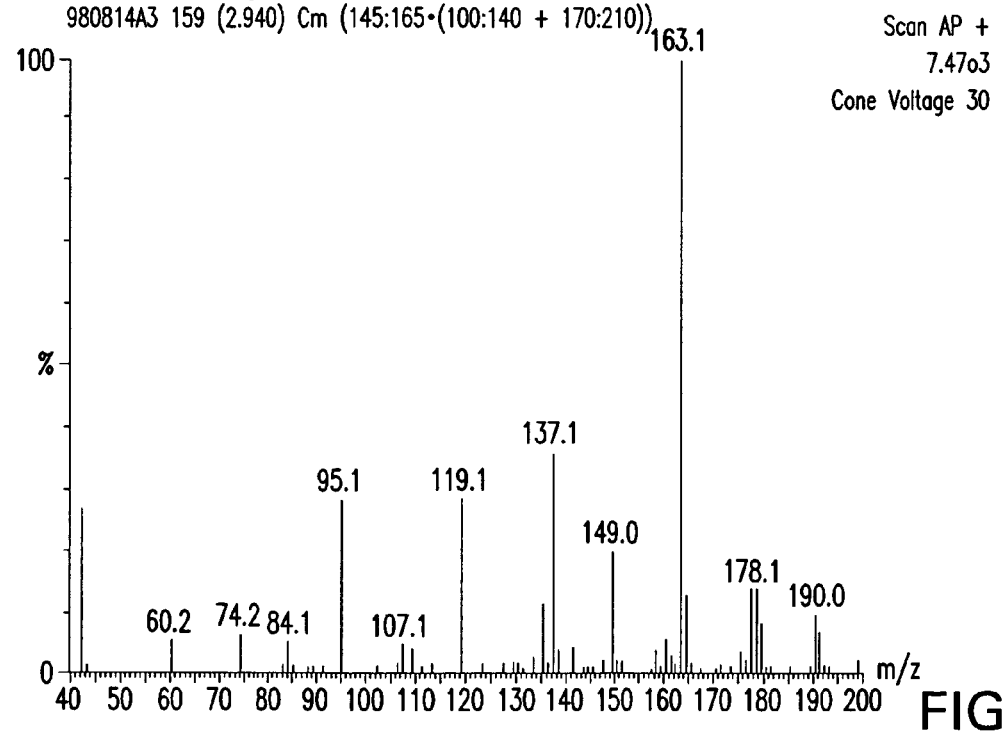
FIG. 5B shows the curve of the re-dissolved sample.
Figure 5C:
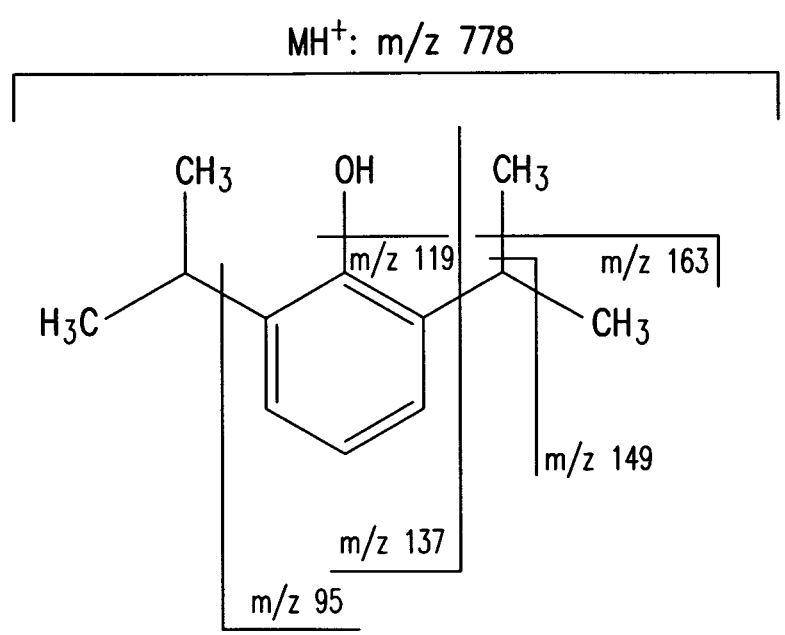
FIG. 5C shows the fragmentation of the propofol.

The substance was determined and found unchanged by LC/MS [J. of Chromatography B, 669: p. 358-365, 1995]. The comparative results are shown in FIG. 5: FIG. 5A shows the mass spectrum of the standard, FIG. 5B shows the curve of the re-dissolved sample. FIG. 5C shows the fragmentation of propofol.

LC/MS parameters:
ionisation: APCI+interface; nitrogen flow rate: 300 l/h; solvent: acetonitrile/water=73/23; flow rate: 0.300 ml/min.

Example II.35

9.0 ml of a 0.8% ($1.213*10^{-4}$ M) solution of HSA and 1.0 ml of a 4.0 mg/ml ($4.33*10^{-3}$ M) solution of amphotericin B in dimethyl formamide were mixed to give a clear solution. This solution was dialyzed against 2.0 liter of water (WFI) at 4° C. for period of 20 hours protected from light.

Using the determination method of Example II.24 the binding was found to be 99.6% representing a 1:3.5 ratio for HSA:amphotericin B.

On repeating the dialysis procedure five times the concentration of DMF in the solution was reduced below its detection limit ($2*10^{-9}$ M).

III. Dosage Forms

Examples III.1 to III.6

Following the procedure for the preparation with lyophilisation as described above an appropriate pharmaceutical formulation is obtained. Re-dissolving the solid in adequate volume of WFI so as to reach the concentration of 20% for HSA the solution arrives to a concentration suitable for therapeutic application as summarised below for some active substances:

| Example | name | conc. mg/ml |
| --- | --- | --- |
| III.1 | amphotericin B | 11.09 |
| III.2 | camptothecin | 6.8 |
| III.3 | carbamazepine | 1.98 |

-continued

| Example | name | conc. mg/ml |
|---|---|---|
| III.4 | cyclosporin A | 0.50 |
| III.5 | paclitaxel | 1.0 |
| III.6 | propofol | 10.0 |

The above dosage forms can be further finished in vials for injectables and infusions.

IV. Biological Examples

Studies on Biological Equivalence

Biological equivalence was determined comparing the new formulations according to the invention with known formulations used in therapy containing the same active substance with poor water solubility. Such known formulations were prepared in polyoxyethylated castor oil (Cremophor EL) and absolute ethanol.

Materials Used:

Paclitaxel dissolved in a mixture of polyoxyethylated castor oil (Cremophor EL): absolute ethanol=1:1, was compared with the aqueous solution of paclitaxel/HSA of the invention, prepared according to Example II.2.

Example IV.1

In vitro Studies

Comparative studies were carried out in vitro to determine the antiproliferative and cytotoxic activity 'on human tumour cell lines. The Cremophor EL/absolute ethanol and HSA formulation of paclitaxel was compared on K562 human myeloid leukaemia, MCF-7 and MDA-231 breast and OVCAR-5 ovarian carcinoma cell lines [Anticancer Research, Vol. 16: p. 2469-2478, 1996.)

Method:

Colony growth inhibition assay: Monolayer cultures of the cell lines were treated with eight different concentrations of the drug in the two above formulations plus in DMSO/saline solution as a reference. The cultures were incubated for 24, 48, 72, 96 and 120 hours respectively. The colonies were stained with crystal violet and the survival of treated cells was calculated as percentage of colonies formed by untreated cells. Tables II A through IV B show the results obtained on the different cell lines. In each study the survival of treated cells is shown, calculated as percentage of colonies formed by untreated cells. All values are the average of three experiments.

TABLE II A cell line: MCF7 breast carcinoma formulation: paclitaxel/Cremophor EL & absolute ethanol

| Pt × cc [uM]\t [h] | 24 h | 48 h | 72 h | 96 h | 120 h |
|---|---|---|---|---|---|
| 0.005 | 92* | 86 | 76 | 42 | 30 |
| 0.01 | 90 | 81 | 72 | 33 | 26 |
| 0.02 | 86 | 71 | 67 | 29 | 23 |
| 0.025 | 84 | 64 | 60 | 24 | 18 |
| 0.05 | 82 | 60 | 52 | 23 | 16 |
| 0.1 | 80 | 57 | 38 | 18 | 15 |
| 1.0 | 68 | 46 | 28 | 15 | 6.5 |
| 10.0 | 62 | 33 | 21 | 10 | 4.6 |

TABLE II B cell line: MCF7 breast carcinoma formulation: paclitaxel/HSA

| Pt × cc [uM]\t [h] | 24 h | 48 h | 72 h | 96 h | 120 h |
|---|---|---|---|---|---|
| 0.005 | 91 | 84 | 75 | 41 | 27 |
| 0.01 | 88 | 81 | 69 | 35 | 23 |
| 0.02 | 84 | 76 | 64 | 31 | 20 |
| 0.025 | 80 | 70 | 59 | 28 | 16 |
| 0.05 | 77 | 66 | 53 | 25 | 12 |
| 0.1 | 75 | 59 | 46 | 20 | 9.5 |
| 1.0 | 67 | 42 | 30 | 17 | 6.2 |
| 10.0 | 58 | 31 | 21 | 9.0 | 3.0 |

TABLE III A cell line: MDA-231 breast carcinoma formulation: paclitaxel/Cremophor EL & absolute ethanol

| Pt × cc [uM]\t [h] | 24 h | 48 h | 72 h | 96 h | 120 h |
|---|---|---|---|---|---|
| 0.005 | 97 | 89 | 80 | 47 | 34 |
| 0.01 | 94 | 87 | 75 | 41 | 30 |
| 0.02 | 89 | 82 | 69 | 37 | 28 |
| 0.025 | 86 | 76 | 65 | 34 | 23 |
| 0.05 | 84 | 72 | 59 | 29 | 21 |
| 0.1 | 83 | 66 | 53 | 26 | 18 |
| 1.0 | 73 | 49 | 34 | 21 | 9.5 |
| 10.0 | 65 | 37 | 24 | 14 | 8.2 |

TABLE III B cell line: MDA-231 breast carcinoma formulation: paclitaxel/HSA

| Pt × cc [uM]\t [h] | 24 h | 48 h | 72 h | 96 h | 120 h |
|---|---|---|---|---|---|
| 0.005 | 92 | 78 | 51 | 30 | 10 |
| 0.01 | 86 | 65 | 38 | 24 | 8.3 |
| 0.02 | 75 | 51 | 33 | 22 | 7.0 |
| 0.025 | 64 | 47 | 28 | 19 | 6.4 |
| 0.05 | 60 | 42 | 26 | 18 | 5.3 |
| 0.1 | 55 | 36 | 24 | 16 | 4.0 |
| 1.0 | 49 | 33 | 22 | 15 | 3.2 |
| 10.0 | 45 | 26 | 20 | 10 | 2.6 |

TABLE IV A cell line: K562 human myeloid leukaemia formulation: paclitaxel/Cremophor EL & absolute ethanol

| Pt × cc [uM]\t [h] | 24 h | 48 h | 72 h | 96 h | 120 h |
|---|---|---|---|---|---|
| 0.005 | 88 | 59 | 30 | 21 | 10 |
| 0.01 | 79 | 40 | 21 | 15 | 8.7 |
| 0.02 | 66 | 31 | 19 | 12 | 7.2 |
| 0.025 | 62 | 29 | 17 | 10 | 6.0 |
| 0.05 | 56 | 25 | 14 | 9.4 | 5.4 |
| 0.1 | 51 | 23 | 12 | 7.7 | 4.6 |
| 1.0 | 47 | 20 | 10.5 | 6.0 | 3.0 |
| 10.0 | 39 | 16 | 9.5 | 4.2 | 2.0 |

TABLE IV B cell line: K562 human myeloid leukaemia sample: paclitaxel/HSA

| Pt × cc [uM]\t [h] | 24 h | 48 h | 72 h | 96 h | 120 h |
|---|---|---|---|---|---|
| 0.005 | 89 | 53 | 31 | 18 | 5.4 |
| 0.01 | 75 | 40 | 22 | 11 | 4.7 |
| 0.02 | 69 | 32 | 18 | 9.0 | 4.0 |

TABLE IV B-continued cell line: K562 human myeloid leukaemia sample: paclitaxel/HSA

| Pt × cc [uM]\t [h] | 24 h | 48 h | 72 h | 96 h | 120 h |
|---|---|---|---|---|---|
| 0.025 | 65 | 30 | 14 | 7.6 | 3.5 |
| 0.05 | 58 | 25 | 11 | 7.0 | 3.0 |
| 0.1 | 53 | 21 | 9.5 | 5.6 | 2.4 |
| 1.0 | 47 | 18 | 8.0 | 5.0 | 1.7 |
| 10.0 | 41 | 16 | 7.1 | 4.7 | 1.0 |

Example IV.2

In Vivo Pharmacokinetic Test

From the therapeutic point of view, the bio-equivalence can be considered, demonstrating equal pharmacokinetic characteristics such as AUC (area under the curve), elimination constants, plasma half life after the administration of the same dose to the same species. Such experiment was done on rats for the two formulations as in Example IV.1. [Semin Oncol, VOL. 21 (5 Suppl. 8): p. 53-62, 1994.].

AUC means the area under the curve on a plasma concentration versus time diagram. It can be generated measuring the plasma concentration of the compound administered at different points of time.

Pharmacokinetic Study on Rats:

Method: The dose of 2.5 mg/kG paclitaxel was administered in 1.0 ml volume i.v. bolus to CR. (Wi) BR rats (body weight between 380 and 420 grams), and a 1.0 ml blood sample was drawn into a heparinised test tube from three animals at each point of time as indicated below:

| # | 0' | 10' | 20' | 30' | 45' | 60' | 90' | 2 h | 3 h | 4 h | 5 h | 6 h |
|---|---|---|---|---|---|---|---|---|---|---|---|---|
| 1 | + | + | + | | | | | | | | | |
| 2 | | + | + | + | | | | | | | | |
| 3 | | | + | + | + | | | | | | | |
| 4 | | | | + | + | + | | | | | | |
| 5 | | | | | + | + | + | | | | | |
| 6 | | | | | | + | + | + | | | | |
| 7 | | | | | | | + | + | + | | | |
| 8 | | | | | | | | + | + | + | | |
| 9 | | | | | | | | | + | + | + | |
| 10 | | | | | | | | | | + | + | + |
| 11 | + | | | | | | | | | | + | + |
| 12 | + | + | | | | | | | | | | + |

The plasma fraction was separated by quick centrifugation at +5° C. and kept frozen at −70° C. until processed for analytical measurement.

Sample preparation: The frozen plasma samples were warmed up to +8° C., centrifuged for 5 min at 5000 RPM. 0.300-0.500 ml of the clear plasma solution was taken out and loaded onto an Oasis HLB 1 cc SPE (Solid Phase) Extraction cartridge. Before the plasma sample was loaded the cartridge was rinsed with 1 ml of methanol, followed by 1 ml water for pre-conditioning. The paclitaxel content absorbed onto the SPE cartridge, while the rest of the sample components were rinsed out with 1 ml of water and 1 ml of 30% acetonitrile/water solution. The cartridge was blown dry by air. Paclitaxel was eluted from the SPE cartridge with 1 ml absolute ethanol. The sample was evaporated to dryness with nitrogen, stored at (−20° C.) for analysis. The residue was dissolved in 0.200 ml absolute ethanol and injected for HPLC analysis.

The HPLC conditions were the same as applied for substance identification.

Results:

The points obtained were the average of three measured from the samples of three individual animals. As a result, the difference between the two curves obtained from the pharmacokinetic study for the equal dose of the two different formulations, remained within the deviation of the individual samples. The same curve takes shape plotting all the individual data, indicating no or minor difference in pharmacokinetic characteristics of the two formulations.

Example IV.3

In viva evaluation of antiproliferative and cytotoxic activity investigations show that the new formulations shows a positive effect against human tumour xenografts CH1 and $CHI_{tax}$ in nude mice.

Example IV.4

Hypersensitivity Tests

About 45% of the patients treated with paclitaxel expressed hypersensitivity reactions. These side effects were proven related to one excipient of the formulation, Cremophor EL, as observed with other pharmaceutical products containing the same component. This hypersensitivity reaction is determined as anaphylactic toxicity expressed through induction of histamine release by Cremophor EL.

Our study was performed on CRL (WI) BR male rats weighing 130-150 g [14]. The administered dose was calculated around 7.0 mg/kG for paclitaxel, given i.v. in 1.0 ml of total volume. A group for each time point and dose contained 5 animals. The blood samples were collected into heparin containing tubes after 2, 5 and 10 minutes of treatment. The plasma was separated by quick centrifugation. The samples were stored at −70° C.

The histamine content of the sample was $C^{14}$-methylated by specific histamine-N-methyl-transferase enzyme. The histamine level was determined in the plasma samples measuring the $C^{14}$ radioactivity in the samples.

The data obtained indicated that Cremophor EL and the containing formulation have substantial histamine release induction, while HSA an the HSA containing formulation and paclitaxel itself do not show any such effect.

Example IV.5

The same phenomenon as in Example IV.4 was found using in vitro human experiments from human blood samples based on the quantitative assay of chromatin activation of blood lymphocytes [Method: Analytical and Quantitative Cytology and Histology, VOL. 8: p. 1, 1986.].

The invention claimed is:

1. A method of treating cancer comprising parenterally administering to a patient in need thereof an organic solvent-free aqueous solution of a pharmaceutical composition comprising:
   a) as active ingredient a therapeutically effective amount of camptothecin; and
   b) human serum albumin;
   where the camptothecin and the human serum albumin are non-covalently bound to each other and where greater than 98% of the camptothecin is bound to the human serum albumin;
   whereby the cancer is treated.

2. A method of treating cancer comprising parenterally administering to a patient in need thereof an organic solvent-free aqueous solution of a pharmaceutical composition comprising:
 a) as active ingredient a therapeutically effective amount of camptothecin; and
 b) human serum albumin;
 where the camptothecin and the human serum albumin are non-covalently bound to each other and where greater than 98% of the camptothecin is bound to the human serum albumin;
 whereby the cancer is treated;
 and where the pharmaceutical composition is obtainable by a process comprising:
  i) dissolving camptothecin in an organic solvent;
  ii) dissolving the human serum albumin in an aqueous solution;
  iii) combining the organic solution of step i) with the aqueous solution of step ii); and
  iv) removing the organic solvent by ultrafiltration, dialyzing, diafiltrating, or lyophilizing;
 where if lyophilizing is used to remove the organic solvent, the solid is dissolved in water or an aqueous solution before administration to the patient.

3. A method of treating cancer comprising parenterally administering to a patient in need thereof an organic solvent-free aqueous solution of a pharmaceutical composition comprising:
 a) as active ingredient a therapeutically effective amount of paclitaxel; and
 b) a plasma protein;
 where the paclitaxel and the plasma protein are non-covalently bound to each other and where greater than 98% of the paclitaxel is bound to the plasma protein;
 whereby the cancer is treated; and
 where the plasma protein is human serum albumin.

4. A method of treating cancer comprising parenterally administering to a patient in need thereof an organic solvent-free aqueous solution of a pharmaceutical composition comprising:
 a) as active ingredient a therapeutically effective amount of paclitaxel; and
 b) a plasma protein;
 where the paclitaxel and the plasma protein are non-covalently bound to each other and where greater than 98% of the paclitaxel is bound to the plasma protein;
 whereby the cancer is treated;
 and where the pharmaceutical composition is obtainable by a process comprising:
  i) dissolving paclitaxel in an organic solvent;
  ii) dissolving the plasma protein in an aqueous solution;
  iii) combining the organic solution of step i) with the aqueous solution of step ii); and
  iv) removing the organic solvent by ultrafiltration, dialyzing, diafiltrating, or lyophilizing to form a solid;
 where if lyophilizing is used to remove the organic solvent, the solid is dissolved in water or an aqueous solution before administration to the patient; and
 where the plasma protein is human serum albumin.

5. The method of claim 2 where the organic solvent is ethanol and the solvent is removed by lyophilization.

6. A method of treating cancer comprising parenterally administering to a patient in need thereof an organic solvent-free aqueous solution of a pharmaceutical composition comprising:
 a) as active ingredient a therapeutically effective amount of paclitaxel; and
 b) a plasma protein;
 where the paclitaxel and the plasma protein are non-covalently bound to each other and where greater than 98% of the paclitaxel is bound to the plasma protein;
 whereby the cancer is treated; and
 where the plasma protein is a human immunoglobulin.

7. The method of claim 1 or 2 where the patient is human and the camptothecin is administered to the patient in a dose of 3-5 mg/kG/day.

8. A method of treating cancer comprising parenterally administering to a patient in need thereof an organic solvent-free aqueous solution of a pharmaceutical composition comprising:
 a) as active ingredient a therapeutically effective amount of paclitaxel; and
 b) a plasma protein;
 where the paclitaxel and the plasma protein are non-covalently bound to each other and where greater than 98% of the paclitaxel is bound to the plasma protein;
 whereby the cancer is treated;
 and where the pharmaceutical composition is obtainable by a process comprising:
  i) dissolving paclitaxel in an organic solvent;
  ii) dissolving the plasma protein in an aqueous solution;
  iii) combining the organic solution of step i) with the aqueous solution of step ii); and
  iv) removing the organic solvent by ultrafiltration, dialyzing, diafiltrating, or lyophilizing to form a solid;
 where if lyophilizing is used to remove the organic solvent, the solid is dissolved in water or an aqueous solution before administration to the patient; and
 where the plasma protein is a human immunoglobulin.

* * * * *